United States Patent
Shinohara et al.

(10) Patent No.: US 7,159,446 B2
(45) Date of Patent: *Jan. 9, 2007

(54) PARTICULATE MATTER CONCENTRATION MEASURING APPARATUS

(75) Inventors: Masayoshi Shinohara, Kyoto (JP); Hiroshi Mizutani, Kyoto (JP)

(73) Assignee: Horiba, Ltd., Kyoto (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/119,123

(22) Filed: Apr. 29, 2005

(65) Prior Publication Data

US 2005/0188746 A1    Sep. 1, 2005

Related U.S. Application Data

(62) Division of application No. 10/602,501, filed on Jun. 24, 2003, now Pat. No. 6,964,190.

(30) Foreign Application Priority Data

| Jun. 28, 2002 | (JP) | ............................. 2002-189201 |
| Aug. 16, 2002 | (JP) | ............................. 2002-237468 |
| Oct. 25, 2002 | (JP) | ............................. 2002-311384 |
| Nov. 1, 2002 | (JP) | ............................. 2002-319882 |

(51) Int. Cl.
*G01N 1/00* (2006.01)
*B32B 27/30* (2006.01)
*B01D 71/36* (2006.01)

(52) U.S. Cl. ...................... 73/28.04; 73/28.05; 55/354

(58) Field of Classification Search ............... 73/28.01, 73/28.04, 28.05, 28.06, 863.22, 863.23

See application file for complete search history.

(56) References Cited

U.S. PATENT DOCUMENTS

| 3,244,287 | A | * | 4/1966 | Staunton et al. ............ 210/387 |
| 3,711,707 | A | | 1/1973 | Lilienfeld et al. |
| 4,011,067 | A | * | 3/1977 | Carey, Jr. .................... 55/354 |
| 4,192,176 | A | | 3/1980 | Barringer |
| 4,464,574 | A | | 8/1984 | Vandrish |
| 4,866,277 | A | | 9/1989 | Johnson et al. |
| 4,941,742 | A | | 7/1990 | Schrader et al. |
| 4,961,916 | A | | 10/1990 | Lessage et al. |
| 5,317,930 | A | | 6/1994 | Wedding |
| 5,349,844 | A | | 9/1994 | Lilienfeld |

FOREIGN PATENT DOCUMENTS

| EP | 1 142 702 A1 | 10/2001 |
| GB | 2 146 430 A | 4/1985 |

(Continued)

OTHER PUBLICATIONS

"PTFE Membrane Filters" data sheet from Millipore Corporation, Bedford, MA, at www.millipore.com, printed May 2001.*

(Continued)

*Primary Examiner*—Michael Cygan

(57) ABSTRACT

A highly sensitive particulate matter concentration measuring apparatus for measuring a concentration of particulate matter in a sample gas collected in a collecting region formed on a collecting medium, the collecting region being formed by drawing the sample gas through a cross-sectional area of the collecting medium, the collecting medium is a filter tape that includes a porous film made of a fluorine resin and a reinforcing layer provided on the porous film, the particulate matter concentration is measured using a beta-ray absorbing method while removing the error influences of naturally occurring beta radiation, and includes an additional impact type sampler or cyclone type sampler for filtering the sample gas prior to collecting the particulate matter in the collecting region.

22 Claims, 16 Drawing Sheets

FOREIGN PATENT DOCUMENTS

| | | |
|---|---|---|
| JP | 09-2111133 | 8/1997 |
| JP | 2000-176262 | 6/2000 |
| JP | 2000-278347 | 10/2000 |
| JP | 2001-347686 | 12/2001 |

OTHER PUBLICATIONS

Horiba Technical Reports: Readont No. 23, "Ambient SPM Monitor APDA—361", Sep. 2001, pp. 43-46; with English Abstract.

* cited by examiner

PARTICULATE MATTER CONCENTRATION MEASURING APPARATUS

CROSS-REFERENCE TO RELATED APPLICATION

This application is a divisional of U.S. patent application Ser. No. 10/602,501 filed on Jun. 24, 2003 and now U.S. Pat. No. 6,964,190.

This application is based on applications 2002-189201, 2002-237468, 2002-311384, and 2002-319882 filed in Japan, the content of which are hereby incorporated by reference.

BACKGROUND OF THE INVENTION

1. Field of the Invention

The present invention relates to a particulate matter concentration measuring apparatus for measuring a concentration of particulate matter in a sample gas, and specifically to a filter tape used for use in measuring the concentration of the particulate matter.

2. Description of Related Art

As an apparatus for measuring particulate matter (hereinafter, refer to as PM) in the atmosphere, there is an apparatus which continuously receives fixed flow rate samples of the atmosphere into a sampling tube (a gas introduction pipe) as a sample gas, continuously collects the PM from the sample gas within a vacuum chamber provided in a downstream side of the sampling tube by using a collecting means such as a filter tape (a ribbon filter) or the like, irradiates beta rays onto the collected PM from a beta-ray source, detects transmitted beta rays at that time by a detector, and measures a concentration of the collected PM in accordance with a beta-ray absorbing method by using an output of the detector.

This PM concentration measuring apparatus has a plurality of exhaust holes for discharging the sample gas passing through the filter tape, and is provided with a supporting means for supporting the filter tape in a state of preventing the filter tape from being deformed during collection of the sample. FIG. 7 shows a structure of a plate-like portion 60 held by a supporting means. The plate-like portion 60 is structured by bonding a thin plate-like portion to a hole portion provided in the supporting means, the plate-like portion 60 has three exhaust holes 61, 62 and 63, and is arranged adjacent to the under face side of a filter tape 64.

The sample gas is drawn by a sampling pump arranged in a under face side of the plate-like portion 60, and passes through the filter tape 64 from the upper face side to the under face side, and through three exhaust holes 61, 62 and 63. The sample gas is drawn through the filter tape and the plate-like portion for a fixed time (for example, one hour), whereby the collecting region is formed on the filter tape 64. Reference numeral 65 denotes a take-up direction of the filter tape 64.

In the case of measuring the concentration of the PM by using the beta-ray absorbing method, the beta rays are irradiated onto the collecting region from a radiation source arranged in a under face side of the plate-like portion 60, and the beta rays passing through the collecting region are detected by a detector arranged in the upper face side of the filter tape 64 via a protection film provided at the inlet of the detector, whereby the detector produces a signal representative of the concentration of the PM. In this case, the protection film has a function of restricting a pressure loss applied to the detector caused by the sample gas suction of the sampling pump.

Meanwhile, in the beta-ray absorbing method, it is desirable that the weight (the density) of the filter tape 64 be small in order to provide increased measurement sensitivity. However, the material of the filter tape 64 is generally glass fiber, and the fixed thickness (450 µm; average value) and a fixed weight (7 mg/cm$^2$; average value) are required in the glass fiber for the purpose of obtaining enough strength to withstand continuous use. Accordingly, since the strength of the filter tape 64 cannot be preserved while reducing the weight (the density) of the glass fiber, such filter tape is undesirable for use in continuous measurement. Further, high sensitivity is difficult to obtain with glass fiber tape since the beta rays are partially absorbed by the glass fiber.

Further, since three exhaust holes 61, 62 and 63 are considerably large, some deformation of the filter tape 64 often occurs partially collapsing the filter tape 64 in these regions during collection of the PM. This deformation may result in slight differences in concentration measurements, making it difficult to obtain reproducible measurement results.

Further, in the PM concentration measuring apparatus of beta-ray absorbing type mentioned above, a proportional counter is generally used as a detector for detecting the transmitting beta rays. Typically, the proportional counter can detect alpha rays as well as beta rays. In the proportional counter, as is understood from transmission distribution curves A and B in FIG. 9, since peaks P$_A$ and P$_B$, in a transmission amount of the alpha rays (shown by the curve A in the drawing) and the beta rays (shown by the curve B in the drawing) are different, there is no problem in most of the spectrum in terms of detecting the alpha rays and the beta rays. However, in the portion shown by reference symbol C in FIG. 9, since the beta rays and the alpha rays overlap in this region, the alpha rays contribute to an error factor only to the degree they overlap the beta rays in the portion C.

Further, alpha rays (radon gas) and beta rays exist in nature in trace quantities. Accordingly, in the case of measuring the concentration of the PM collected in accordance with the beta-ray absorption method, any radioactive materials other than the beta-ray source (a sealed ray source) within the measuring apparatus may contribute to an error factor and make it difficult to accurately measure the PM in accordance with the beta-ray absorption detection method.

Meanwhile, it is desirable to measure even the minute PM having a particle diameter equal to or less than 2.5 µm (hereinafter, refer to as PM2.5) at a high sensitivity. However, since an error influence by the alpha rays with respect to the beta rays and an error influence by the beta rays existing in the nature generate a great obstacle in the case of measuring the PM2.5 at a high sensitivity, it is desired to make these influences as small as possible.

FIG. 15 shows a state in which a conventional PM concentration measuring apparatus 120 for measuring PM in a sample gas is in place. This PM concentration measuring apparatus 120 continuously draws in a fixed flow rate of sample gas into a sampling tube and continuously collects the PM within the sample gas S in a chamber provided in a downstream side of the sampling tube by using a collecting means, for example, a ribbon-like filter or the like, and measures the concentration of the collected PM in accordance with the beta-ray absorbing method.

The PM concentration measuring apparatus 120 is, for example, placed in a room, and an introduction port for the sample gas S is communicated and connected to a sampling pipe 102 constituted by a synthetic resin hose communicating with a sample gas introduction portion 102a, for example, provided in a rooftop portion, whereby it is possible to draw in the sample gas S in the open air and measure the PM concentration by the PM concentration measuring apparatus 120 in the room. Further, a cyclone type sampler is installed within the PM concentration measuring apparatus 120 so as to constitute a sizing device for collecting the PM contained in the sample gas S. In this case, the cyclone type sampler in the present specification corresponds to a sampling apparatus (a cyclone type volume sampler) for sizing the PM by using a centrifugal separation caused by an eddy current of the sample gas S, and may be simply referred to as a cyclone in the following description.

FIG. 16 shows an impact type sampler 121 corresponding to the sizing device which is designated as a standard in the U.S. and Europe and an example of a PM concentration measuring apparatus using the impact type sampler 121. In this case, the impact type sampler in the present specification indicates a suction sampler (an impact type low volume sampler) removing the PM having a large particle diameter on the basis of collision of the sample gas S and selectively sampling the PM having a small particle diameter. In the following description, this impact type sampler may be simply called as an impacter. This impacter 121 has a sizing device main body 105 collecting the PM having a large particle diameter equal to or more than 2.5 µm from all the PM removed from the sample gas S, and an introduction portion 122 for the sample gas S to the sizing device main body 105.

FIG. 17 is a view showing a structure of the introduction portion 122 in the impacter 121 mentioned above in an enlarged manner. In FIG. 17, reference numeral 109 denotes a funnel-shaped sample intake port portion formed in an upper end portion of the sizing device main body 105, reference numeral 110 denotes a mounting flange formed in the sample intake port portion 109, reference numeral 111 denotes a clip plate screwed in the mounting flange 110, for example, using threaded holes formed at an interval of 90 degrees, reference numeral 123 denotes a guide body mounted by a fixed interval to the clip plate 111 by using a spacer 124, and reference numeral 125 denotes an annular net-like body clamped between the guide body 123 and the clip plate and provided for the purpose of preventing insects or the like from being mixed. These members 111 to 125 form the introduction portion 122.

Meanwhile, in recent years, taking into consideration that the cyclone has a defect in a low collecting efficiency of the fine particles such as the PM2.5, the Japanese Environmental Agency issued a study entitled "Preliminary Manual for Method of Measuring Mass Concentration of Particulate Matter (PM2.5) in the Atmosphere" in September 2000, and preliminarily employing the impacter 121 for selectively sizing the fine particles having a diameter equal to or less than 2.5 µm, as shown in FIGS. 16 and 17.

However, in the impacter 121, it is necessary that the introduction portion 122 is exposed to the open air. Accordingly, in the case that the impacter 121 mentioned above is employed in the inflow portion of the sample gas S in the PM concentration measuring apparatus 120, it is necessary to place the PM concentration measuring apparatus 120 in a state in which the PM concentration measuring apparatus 120 is held in a support stand 125 having such durability as to be capable of being placed in the open air, as shown in FIG. 16. Or, in the case that the PM concentration measuring apparatus 120 is arranged in the room, it is necessary that the impacter 121 is exposed to the open air by piercing holes for mounting the impacter 121 on a ceiling portion, or by mounting the impacter 121 to an existing atmospheric air introduction portion 102a as shown in FIG. 15.

In any event, it is necessary to perform the mounting which may require a significant cost and time for the purpose of changing the specification of the sizing device, delaying spreading of the sampling of the PM as mentioned in the "Preliminary Manual for Method of Measuring Mass Concentration of Minute Particulate Matter (PM2.5) in Atmospheric Air" above.

Further, as shown in FIG. 17, the introduction portion 122 of the conventional impacter 121 introduces the peripheral air as the sample gas S from all angles (360 degrees) in view of structure, and in order to sufficiently achieve the sizing performance of the sizing device main body 105, it is necessary to introduce the sample gas S evenly, to be taken in from the periphery into the sizing device main body 105 in a state of rectifying the sample gas S so as to change direction downward as shown by the arrow A by the guide body 123.

Therefore, it is difficult to mount a filter (for example, an HEPA filter or the like) for removing the PM in the introduction port portion 122 of the impacter 121. Further, it is difficult to carry out a base line test as a basic instruction (confirmation of noise) in a non-dust state corresponding to an important test for confirming a basic performance of the PM concentration measuring apparatus 120. Accordingly, in the case of carrying out the base line test, it is necessary to take the impacter 121 out from the PM concentration measuring apparatus 120, and directly connect the filter to the PM concentration measuring apparatus 120.

SUMMARY OF THE INVENTION

The present invention discloses a PM concentration measuring apparatus for accurately measuring a concentration of the PM in the sample gas collected in a collecting region by drawing the sample gas to flow through a cross-sectional area of a filter medium at the collecting region and measuring the concentration of PM. The filter medium comprises a filtering means that is a filter tape that is a part of an elongated ribbon mounted on a supply and take-up reel. However, the filter medium may instead be an individual, one-use piece of filter material with the properties herein described that is manually inserted for each test.

A first aspect of the present invention is achieved by providing a PM concentration measuring apparatus that can carry out a measurement having a higher sensitivity and a filter tape used for measuring a concentration of a PM that makes it possible to carry out a measurement having a higher sensitivity.

A second aspect of the present invention is achieved by providing a PM concentration measuring apparatus which can obtain a result of measurement having a high accuracy by eliminating the error influences on the measurement of PM concentration by the minute alpha rays and beta rays existing in nature.

A third aspect of the present invention is to provide a PM concentration measuring apparatus which can be easily placed by employing an impact type sampler designated for a PM2.5 measurement as a sizing device, and to which a filter for carrying out a base line test may be attached.

In order to achieve the aspects mentioned above, and in accordance with a first aspect of the present invention, there is provided a PM concentration measuring apparatus for measuring a concentration of a PM in the sample gas collected in a collecting region which is formed on a filter tape for measuring the concentration of PM by the sample gas being drawn through the filter tape from one face side to another face side, wherein the filter tape is constituted of a porous film made of a fluorine resin for trapping the PM in the sample gas, and a reinforcing layer provided on the porous film. The reinforcing layer passes or transmits the sample gas, and is in that sense "breathable." Although reference is made herein to measuring a PM concentration in a sample gas where the sample is taken from the atmosphere, the present invention is not limited to this application and may well be applied to measuring the PM concentration in a sample taken from another environment.

Further, in accordance with the first aspect of the present invention, there is provided a PM concentration measuring apparatus for measuring a concentration of PM in the sample gas collected on a collecting member in a collecting region. The collecting member is a filter tape, and the collecting region is formed by the sample gas being drawn through the filter tape from one face side to another face side. The filter tape is supported by a supporting means which has a plurality of exhaust holes for discharging the sample gas passing through the filter tape while supporting the filter tape by preventing the filter tape from being deformed at the collecting time. The number of the exhaust holes is equal to or more than four, and the exhaust holes are disposed with approximately circular symmetry around a predetermined central position. As shown in FIG. 4, the exhaust holes may be formed as a honeycomb shape with a central exhaust hole surrounded by other exhaust holes that are distributed with approximately circular or point symmetry about a central point or position.

Further, as the filter tape used for measuring the concentration of the PM in accordance with the first aspect of the present invention, there is provided a filter tape constituted of a porous film made of a fluorine resin, and a reinforcing layer provided on the porous film, wherein the reinforcing layer consists of a non-woven fabric having a low hygroscopic property such as a polyethylene, a polyethylene terephthalate, a nylon, a polyester, a polyamide and the like.

Further, in order to achieve the aspect mentioned above, in accordance with a second aspect of the present invention, there is provided a PM concentration measuring apparatus constituted so as to continuously draw a fixed flow rate of a sample gas into a sampling tube, continuously collect the PM in the sample gas within a chamber provided in a downstream side of the sampling tube by using a collecting means, irradiate beta rays onto the collected PM from a beta-ray source, detect transmitted beta rays at that time by a detector, and measure a concentration of the collected PM in accordance with a beta-ray absorbing method by using an output of the detector, wherein an error influence caused by alpha rays and beta rays existing in nature is removed from the detected value of the beta rays in the detector by subtracting the background amount of alpha rays which are detected in nature.

In particular, the alpha rays (radon gas) are always detected in addition to the beta rays used for a main measurement, by the detector, and a correction coefficient $F_1$ is prepared on the basis of calculation by using the amount of alpha rays obtained by the detection, and an amount of the alpha rays (radon gas) in a portion shown by reference symbol C in FIG. 9 is calculated by using the correction coefficient $F_1$. Further, with respect to the beta rays existing in nature, a correction coefficient $F_2$ is prepared on the basis of calculation by using the amount of the detected alpha rays, and an amount of the beta rays existing in nature is calculated by using the correction coefficient $F_2$. Further, the error values respectively caused by the alpha rays and the beta rays are cancelled by subtracting the error values from the amount of beta rays obtained by the detector. In accordance with this structure, it is possible to remove the error influence caused by the alpha rays and the beta rays existing in nature, obtain a value of transmission beta rays with high accuracy in the PM concentration measuring apparatus of the beta ray absorbing type, and accurately measure the PM by performing an arithmetic operation of the value of transmission beta rays in accordance with a predetermined arithmetic expression.

In order to achieve the aspects mentioned above, in accordance with a third aspect of the present invention, there is provided a PM concentration measuring apparatus, comprising an impact type sampler having a sample introduction portion forming a pipe connection portion in a center portion and capable of introducing a sample gas just downward, and a measurement portion measuring a concentration of the PM in the sample gas passing through the impact type sampler.

Accordingly, in the case of using the PM concentration measuring apparatus in accordance with the present invention, it is possible to test the PM having the particle diameter equal to or less than 2.5 µm using the impact type sampler, only by connecting the pipe generally existing in Japan to the pipe connection portion. That is, neither major piping work nor placing work of the impact type sampler are required at that time for employing the impact type sampler in a sizing device of the PM concentration measuring apparatus.

Further, since the pipe connection portion is formed in a center portion of a cover body, the sample gas introduced via the pipe can be securely introduced just downward, and the sizing device main body 105 can sufficiently achieve a predetermined sizing performance.

In the case that the PM concentration measuring apparatus has a mounting flange for mounting the sample introduction portion to the sample intake portion of the impact type sampler, the sample introduction portion is a cover body having approximately the same outer shape as an outer shape of the mounting flange, and forming the pipe connection portion in a center portion thereof, and the pipe connection portion is a taper-shaped receiving port, it is possible to mount the cover body to the sample intake portion of the conventional impact type sampler, form the pipe connection portion without substantially changing the shape of the existing impact type sampler, and easily mount the pipe to the taper-shaped receiving port.

That is, since no great pressure is applied to the pipe connection portion and a flow passage for the sample gas formed by the pipe connected thereto, it is sufficient to maintain an air-tight seal because the sample gas is the atmospheric air, and the current pipe is a flexible hose-like member, it is not necessary to form a screw-type connection portion in order to obtain a strong air-tight seal. It is useful that the connection of the pipe may be easily replaced by making the structure of the pipe connection portion a tapered receiving port.

In the case that a filter capable of introducing the sample gas containing no dust into the impact type sampler is detachably mounted to the pipe connection portion, it is possible to mount the filter to the impact type sampler without removing the impact type sampler from the main body of the PM concentration measuring apparatus, and it is possible to carry out a base-line test of the PM concentration measuring apparatus by removing the PM from the sample gas.

In the case that the cyclone type sampler is built-in, and a pipe for detachably connecting the impact type sampler to a downstream side of the cyclone type sampler is formed, it is possible to use the cyclone type sampler as the sizing device, expand a range for making good use of the PM concentration measuring apparatus, and also switch into the measuring using the cyclone type sampler in the future in order to compare the results of the measurements of the PM using both sizing devices.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

FIGS. 12A and 12B show a portion of the PM concentration measuring apparatus, in which FIG. 12A is a plan view and FIG. 12B is a vertical cross sectional view;

DETAILED DESCRIPTION OF THE PREFERRED EMBODIMENTS

Reference will now be made in detail to the preferred embodiments of the invention, examples of which are illustrated in the accompanying drawings. While the invention will be described in conjunction with the preferred embodiments, it will be understood that they are not intended to limit the invention to these embodiments. On the contrary, the intention is intended to cover alternatives, modifications and equivalents, which may be included within the spirit and scope of the invention as defined by the appended claims. Furthermore, in the following detailed description of the present invention, numerous specific details are set forth in order to provide a thorough understanding of the present invention. However, it will be obvious to one of ordinary skill in the art that the present invention may be practiced without these specific details. In other instances, well known methods, procedures, components, and circuits have not been described in detail as not to unnecessarily obscure aspects of the present invention.

FIGS. 1 to 6 show one embodiment of a PM concentration measuring apparatus D in accordance with the first aspect of the present invention. In this embodiment, there is shown an example in which a correction in accordance with a combination of a beta-ray absorbing method and a light scattering method is applied to a measurement of the concentration of the PM.

Figure 1:
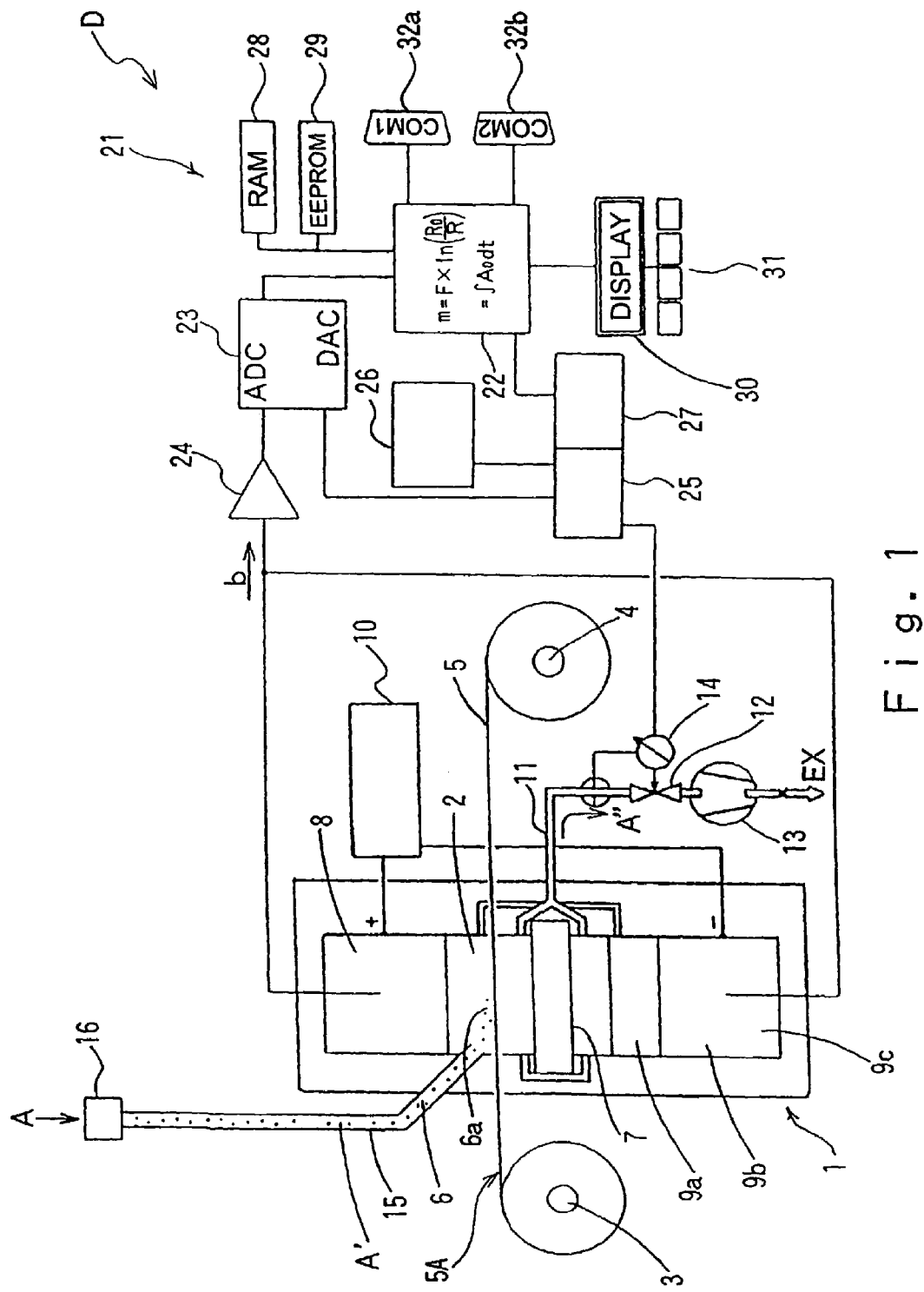
FIG. 1 is a view showing the entire structure of the PM concentration measuring apparatus of the present invention.

FIG. 1 schematically shows one example of an entire structure of the PM concentration measuring apparatus D in accordance with the first aspect of the present invention, and in FIG. 1, reference numeral 1 denotes a measuring apparatus main body. The measuring apparatus main body I is constituted in the following manner. That is, reference numeral 2 denotes a chamber. A filter tape 5 corresponding to a collecting means with a suitable width which is reeled out from a supply reel 3 and is taken up around a take-up reel 4 runs through an inner portion of the chamber 2, a beta-ray source 7 irradiating beta rays onto an accumulated layer 6a of a PM 6 collected on one face (an upper face) of the filter tape 5 is provided in one side (a lower side) of the filter tape 5, and a detector 8, for example, constituted by a proportional counter detecting the beta rays passing through the accumulated layer 6a and outputting a signal in correspondence to a strength of the beta rays is provided in another side (an upper side) thereof, whereby a concentration of the PM 6 can be measured in accordance with a beta-ray absorbing method. In this case, reference symbols 9a and 9b denote compensation chambers. Reference numeral 10 denotes a power source applying a predetermined d.c. voltage to a portion between the detector 8 and the compensation chamber 9b.

Further, reference numeral 11 denotes sample gas exhaust tube which is the exhaust for the chamber 2 and the compensation chamber 9a in a predetermined vacuum state. The sample gas exhaust tube 11 is connected to a sampling pump 13 such as a vacuum pump or the like through a gas flow rate regulator 12, and is provided with a gas flow rate meter 14 for measuring a flow rate of the sample gas A.

Reference numeral 15 denotes a sampling tube supplying a fixed flow rate of sample gas A' to the chamber 2.

A sizing device 16 is provided at the extreme upstream end of the sampling tube 15. The sizing device 16 is structured such as to classify the PM 6 contained in the sample gas A so as to draw into the sampling tube 15, thereby collecting the PM 6 having a particle diameter greater than a predetermined particle diameter and selectively passing the PM 6 having a particle diameter equal to or less than the predetermined particle diameter through the side of the chamber 2.

Meanwhile, the sizing device 16 can employ, for example, a cyclone type volume sampler (which is generally referred to simply as a cyclone) carrying out sizing by utilizing centrifugal separation due to an eddy current in the sample gas S, or an impact type low volume sampler (which is generally referred to simply as an impacter) selectively sampling the PM 6 having a small particle diameter on the basis of collisions in the sample gas S.

Reference numeral 21 denotes an arithmetical control portion controlling the measuring apparatus main body 1 and processing the signals from the side of the measuring apparatus main body 1, reference numeral 22 denotes an arithmetical operation portion performing various kinds of arithmetical operations. Reference numeral 23 denotes a signal converter converting an analogue signal into a digital signal and converting a digital signal to an analogue signal. Reference numeral 24 denotes an amplifier to which an output of the detector 8 is input. Reference numeral 25 denotes an analogue I/O to which detected outputs from the gas flow rate meter 14 and the other sensor 26 are input. Reference numeral 27 denotes a digital I/O. Reference numeral 28 denotes a Random Access Memory (RAM). Reference numeral 29 denotes an electrically erasable programmable (EEPROM). Reference numeral 30 denotes a display portion displaying an arithmetical result and the like. Reference numeral 31 denotes an input keypad. Further, reference symbols 32a and 32b denote COM1 and COM2 corresponding to communication ports for communicating with an external terminal.

Figure 2:
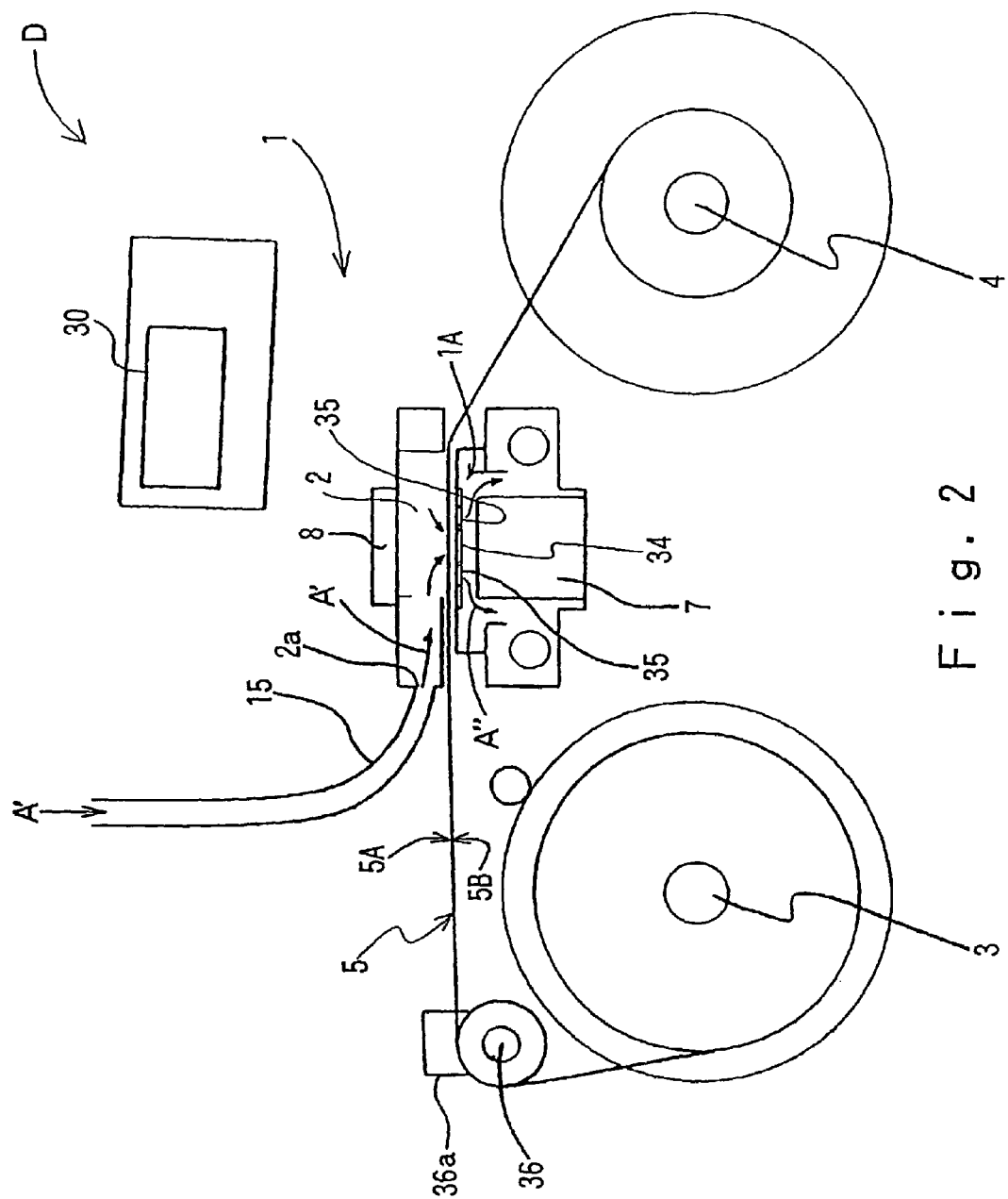
FIG. 2 is a schematic view of the measurement apparatus body.
Figure 3:
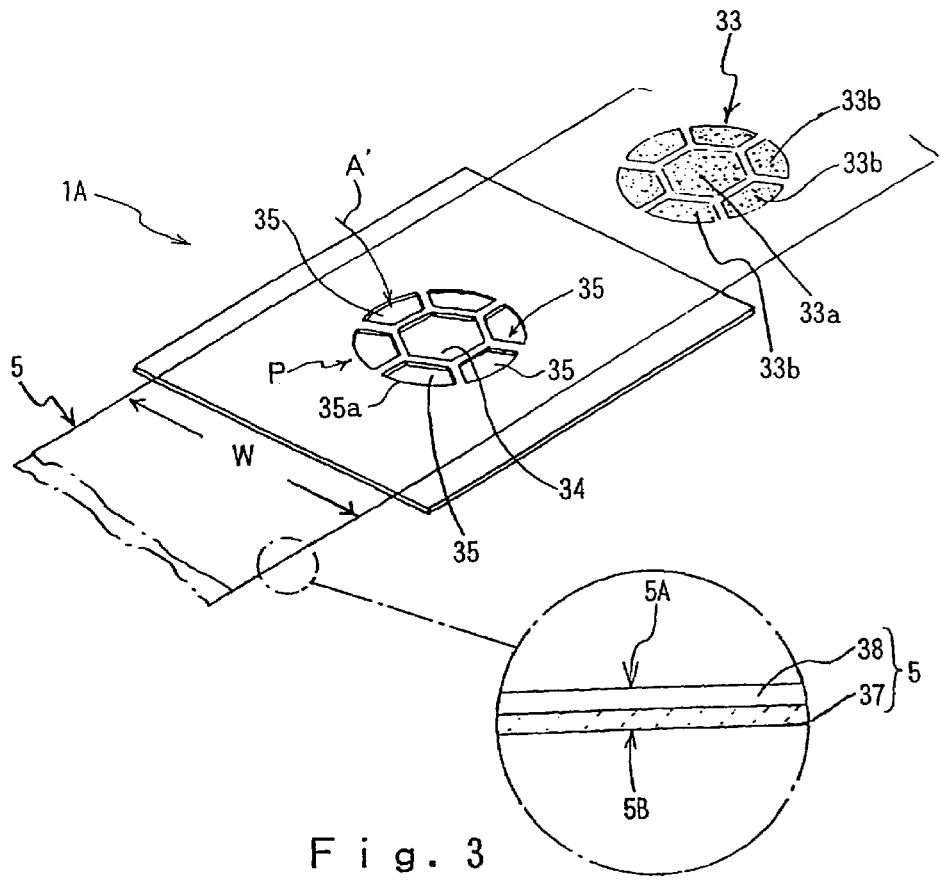
FIG. 3 shows the process of forming a collecting region in accordance with the embodiment mentioned above.
Figure 4:
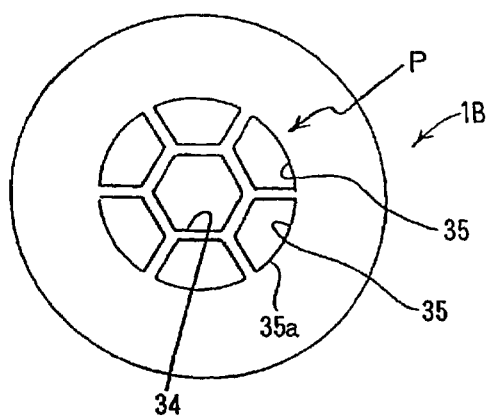
FIG. 4 shows a plan view of a plate-like portion used in the embodiment mentioned above.

FIGS. 2 to 4 show in an enlarged view of the structure of the measuring apparatus main body 1 corresponding to a main portion of the PM concentration measuring apparatus D, in which FIG. 2 is a view showing the structure of the measuring apparatus main body 1, FIG. 3 is a view schematically showing the structure of the collecting medium which is a filter tape 5 and a supporting means 1A thereof corresponding to a main portion of the measuring apparatus main body 1, and FIG. 4 is a view showing in detail the structure of the plate-like portion 1B constituting the supporting means 1A. Alternatively, the collecting medium may also be called a collecting member, and may be a segment-like portion of filter tape material that is not mounted on a supply reel or take-up reel.

As shown in FIG. 2, in the measuring apparatus main body 1 in accordance with the present embodiment, the chamber 2 has the detector 8 in an upper face side 5A (one face side) of the filter tape 5, and is provided with the sampling pump 13 and the beta-ray source 7 in a under face side 5B (another face side) of the filter tape 5. Further, the thin wall plate-like portion 1B formed in the supporting means 1A is arranged between the filter tape 5 and the beta-ray source 7.

An inlet 2a of the chamber 2 is communicated with the sizing device 16 corresponding to a volume sampler (a fixed amount sampling means) via the sampling tube 15, and an outlet of the chamber 2 is communicated with the sampling pump 13 (refer to FIG. 1) via the sample gas exhaust tube 11. The sample gas A is introduced into the sizing device 16 in accordance with the suction of this sampling pump 13, the sample gas A' having a concentration of the PM 6 that is elevated on the basis of the operation of the sizing device 16 and is fed into the chamber 2 via the sampling tube 15 and the inlet 2a, and further, the sample gas A' fed into the chamber 2 is discharged from an inner side of the chamber 2 on the basis of the vacuum created by the sampling pump 13.

At this time, as shown in FIG. 1, the sample gas A' containing the PM 6 having the particle diameter equal to or less than the predetermined particle diameter and drawn into the sampling tube 15 is fed into the chamber 2 provided in a downstream side of the sizing device 16, and passes through the filter tape 5 from the upper face side 5A (one face side) to the under face side 5B (another face side). At this time, the PM 6 in the sample gas A' is collected by the filter tape 5 so as to form a collecting region 33 step-by-step, as shown in FIG. 3. That is, the structure is made such that the sample gas A' passes through four or more exhaust holes such as the central exhaust hole 34, and several peripheral exhaust holes 35 which are formed in the plate-like portion 1B of the supporting means 1A. In this case, reference symbol A" denotes sample gas passing through the central exhaust holes 34, and peripheral exhaust holes 35.

Accordingly, the chamber 2 forms a space for collection and measurement, for the purpose of irradiating the beta rays onto the accumulated layer 6a of the PM 6 formed in the collecting region 33 mentioned above so as to measure the concentration of the PM 6 on the basis of the transmission amount. Further, the transmission of the sample gas A' is kept for a fixed time (for example, one hour), whereby the collecting region 33 corresponding to the amount of the PM 6 contained in the atmosphere A' is formed in the filter tape 5.

On the other hand, the beta rays from the beta-ray source 7 irradiate from just below the plate-like portion 1B in the under face side 5B (another face side) of the filter tape 5, and are passed through the central exhaust hole 34, and peripheral exhaust holes 35, and the beta rays passing through the collecting region 33 formed on the filter tape 5 are detected by the detector 8 positioned just above the collecting region 33 in the upper face side 5A (one face side) of the filter tape 5.

That is, the beta rays mentioned above are exposed to absorption by the PM 6 forming the accumulated layer 6a on the filter tape 5. However, when the beta rays passing through them are detected by the detector 8, an output (an instantaneous value) b in proportion to the incident beta rays is output from the detector 8, whereby it is possible to determine a concentration ($\mu g/m^3$) of the PM 6 contained in the sample gas A. Further, results of measurement are displayed on the display portion 30.

As shown in FIG. 2, the filter tape 5 is constituted such as to pass through the chamber 2 from a reel 36 with a transfer sensor during a period that the filter tape 5 is fed to the take-up reel 4 from the supply reel 3. The reel 36 has a transfer sensor 36a detecting a matter that the filter tape 5 is taken up at a fixed length.

As shown in FIG. 3, the filter tape 5 has, for example, a length of about 40 m, and has a width W of about 4 cm. The filter tape 5 used for measuring the PM concentration is comprised of a porous film 37 is made of a fluorine resin (for example, a tetrafluoroethylene resin) sandwiched together with a reinforcing layer 38 provided on the porous film 37. The filter tape 5 is used in a state in which the reinforcing layer 38 is positioned in the upper face side 5A (one face side) and the porous film 37 is positioned in the under face side 5B (another face side).

The reinforcing layer 38 is constituted of a non-woven fabric having a low hygroscopic property and made of any one of a polyethylene, a polyethylene terephthalate, a nylon, a polyester and a polyamide, and the reinforcing layer 38 is partially attached to the porous film 37 by a predetermined means. Here, the low hygroscopic property in this case means that the reinforcing layer 38 does not attach moisture content causing the absorption of the beta rays. In other words, the reinforcing layer 38 has a hydrophobic nature and is water repellent.

It is preferable that a thickness of the porous film 37 is between 80 and 90 µm. Further, it is preferable that a weight of the porous film 37 is 0.1 to 1 $mg/cm^2$, and it is more preferable that it is about 0.3 $mg/cm^2$. Further, it is preferable that a weight of the reinforcing layer 38 attached to the porous film 37 is between 1 and 2 mg/cm$^2$, and it is preferable that it is set, for example, about 1.2 mg/cm$^2$.

It is preferable that a thickness of the filter tape 5 is between 100 and 200 μm in an average value, and it is considered that the filter tape 5 is structured such as to have a thickness of about 140 μm, in one embodiment. Further, it is preferable that a weight of the filter tape 5 is between 1.1 and 3 mg/cm$^2$ in an average value, and it is considered that the filter tape 5 is structured such as to have a weight of about 1.5 mg/cm$^2$.

Figure 5:
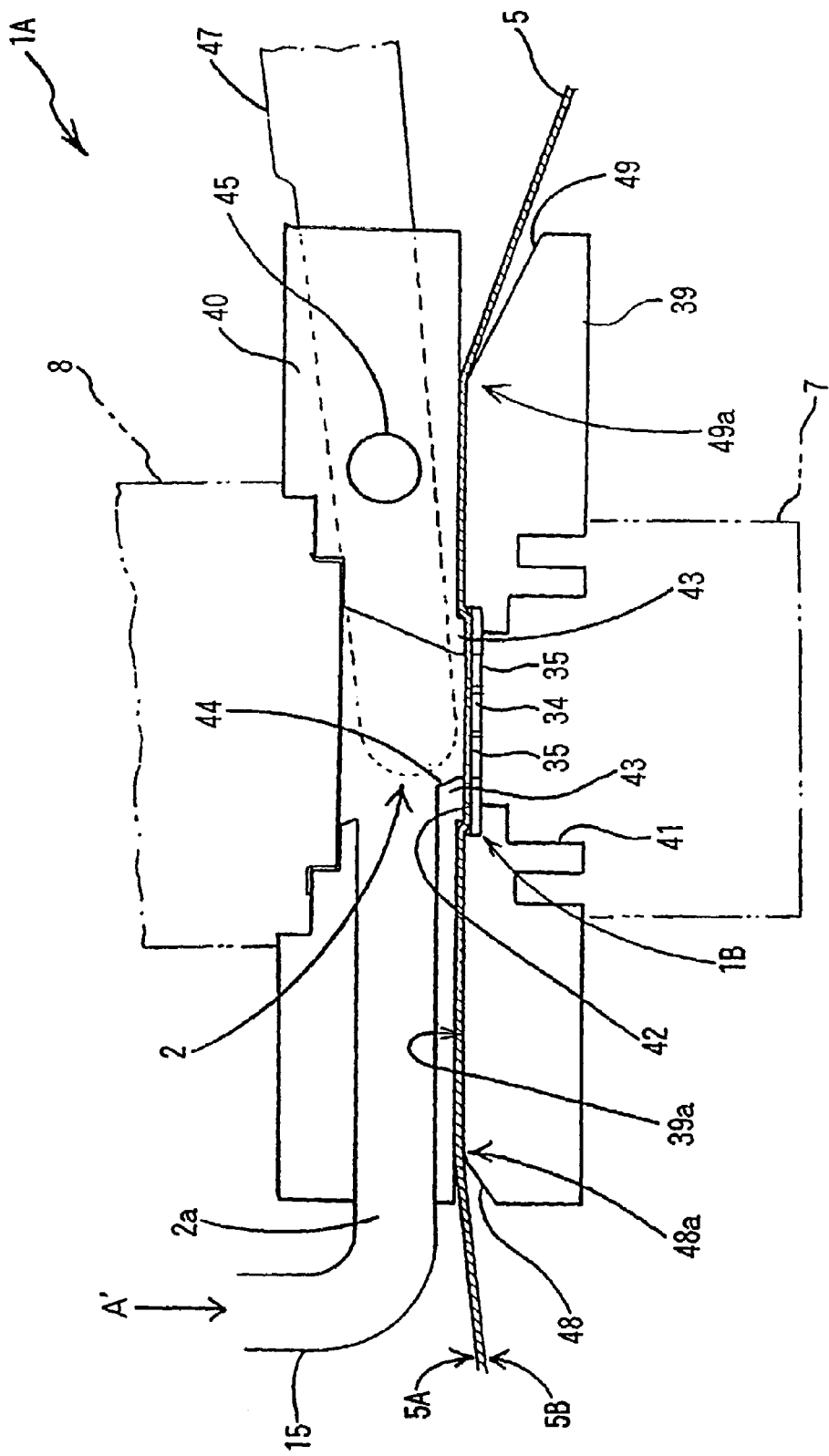
FIG. 5 shows a cross-sectional view of the structure of the supporting means including the plate-like portion.
Figure 6:
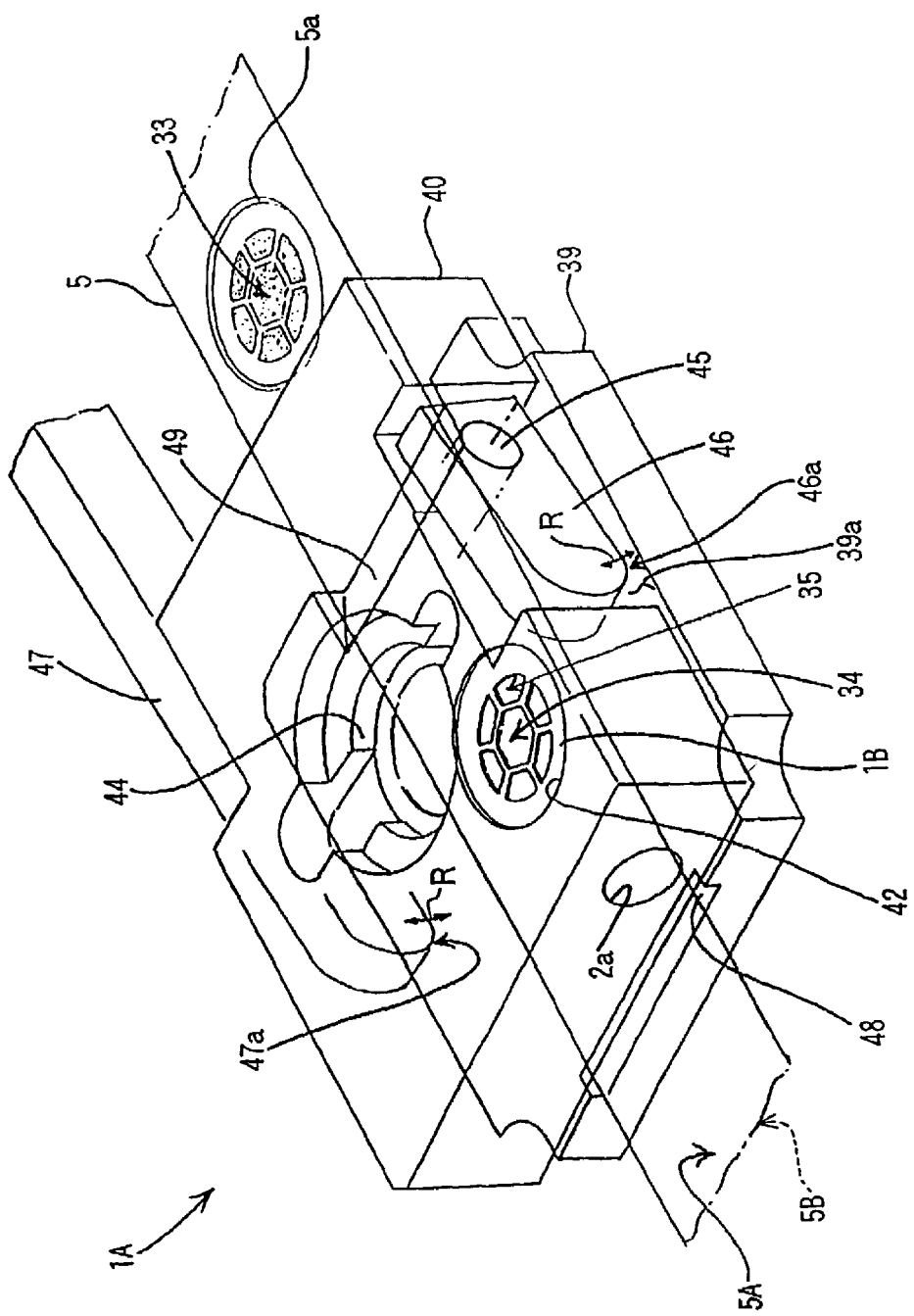
FIG. 6 shows a perspective view of the supporting means.

FIG. 4 is a plan view showing the plate-like portion 1B of the supporting means 1A, and FIGS. 5 and 6 are views showing a detailed structure of the supporting means 1A. The supporting means 1A in accordance with the present embodiment consists of two block-shaped lower clamping means 39 and upper clamping means 40 which are closely attached to each other so as to clamp the filter tape 5 at a time of collecting the PM 6 sample in the filter tape 5 and which are moved apart from each other so as to release the filter tape 5 after collection.

The lower clamping means 39 forms a through hole 41 for being continuously provided with the beta-ray source 7 in a lower side thereof, and the thin plate-like portion 1B, for example, made of an aluminum is welded in such a manner as to close the through hole 41. This plate-like portion 1B is constituted such as to support the filter tape 5 in a state of preventing the filter tape 5 from being deformed to the under face side (another face side) at a time of collecting, and is formed, for example, in a disc shape as shown in FIG. 4, and is provided so as to be arranged just below the filter tape 5 within the chamber 2.

Further, the plate-like portion 1B is formed as a recess portion 42 which is somewhat (about some hundreds μm) recessed with respect to an upper face 39a of the lower clamping means 39 as shown in FIGS. 5 and 6, and a convex portion 43 preventing the filter tape 5 from being displaced by being fitted into the recess portion 42 is formed in a corresponding portion of the upper clamping means 40. That is, the recess portion 42 of the lower clamping means 39 and the convex portion 43 of the upper clamping means 40 are fitted, whereby the filter tape 5 is clamped between an inner periphery of the recess portion 42 and an outer periphery of the convex portion 43 and deformed so as to form a deformed portion 5a. The displacement can be securely prevented by engagement among the deformed portion 5a, the recess portion 42 and the convex portion 43.

Further, a through hole 44 which has the same width as or is wider than the corresponding portion to the central exhaust hole 34, an peripheral exhaust holes 35 is formed in a center portion of the convex portion 43, and the structure is made such that the exhaust holes (34, 35) are communicated with the inner side of the chamber 2 via the filter tape 5. Further, the structure is made such that a depth of the recess portion 42 is slightly shallower than a height of the convex portion 43. Accordingly, the filter tape 5 is securely clamped by the convex portion 43 and the plate-like portion 1B in outer sides of the exhaust holes (34, 35) and a position thereof can be completely held.

That is, it is possible to more strictly define the collecting region 33 formed by the exhaust holes (34, 35) by doing away with the displacement of the filter tape 5, and it is possible to improve an accuracy of measurement and secure a reproducibility at that degree. Meanwhile, it can be easily considered that a positional relationship between the recess portion 42 and the convex portion 43 may be reversed.

In addition, the upper clamping means 40 is provided with a pair of separation levers 46 and 47 which are tilted around an axial core 45 as shown by both arrows R, whereby leading end portions 46a and 47a are brought into contact with the upper surface 39a of the lower clamping means 39, and which are pressed down, whereby a force can be applied in a direction of detaching the fitting between both clamping means 39 and 40. Further, the lower clamping means 39 is energized to a side of the upper clamping means 40 by an energizing means (not shown). That is, the fitting and the separation between both clamping means 39 and 40 can be freely controlled by tilting the separation lever 47 in the directions shown by both arrows R by means of an actuator (not shown).

Further, since the separation levers 46 and 47 are provided, it is possible to detach the fitting between both clamping means 39 and 40 by applying a principle of leverage. That is, even when the fitting between the recess portion 42 and the convex portion 43 is strong, it is possible to easily separate the engagement between both clamping means 39 and 40 on the basis of the operation of the actuator.

Reference numerals 48 and 49 in FIGS. 5 and 6 denote a notch formed so as to guide the filter tape 5 in a lateral direction in a portion in which the lower clamping means 39 and the filter tape 5 are in contact, and make angles of corner portions 48a and 49a contact with the filter tape obtuse. That is, even when taking up the filter tape 5 in a state of applying tension to the filter tape 5, the filter tape 5 can be protected by somewhat rounding the corner portions 48a and 49a by the notches 48 and 49.

Further, a shape of the plate-like portion 1B and a shape of the recess portion 42 and the convex portion 43 are formed in a disc shape. Accordingly, a tensional force generated in the filter tape 5 by forming the deformation portion 5a, and a pressure generated by fitting the recess portion 42 to the convex portion 43 are applied evenly to the filter tape 5 and the plate-like portion 1B, and a deflection or the like is hardly generated in the plate-like portion 1B itself. However, the shape of the plate-like portion 1B may be a thin plate body having a rectangular shape in a plan view as shown in FIG. 3. Further, in order to minimize the deformation, it is desirable that the plate-like portion 1B is a thin portion formed a part of the lower clamping means 39.

Here, in the case that the plate-like portion 1B is independently formed from the lower clamping means 39 as in the present embodiment, it is desirable that an exhaust hole pattern P formed by the respective exhaust holes (34, 35) can be selected by making the plate-like portion 1B replaceable. That is, it is possible to set the exhaust hole pattern P on the basis of the particle diameter of the PM 6 to be measured by replacing the plate-like portion 1B. Further, it is desirable that the exhaust hole pattern P is formed with circular symmetry around a predetermined position, that is, a center point of the exhaust hole 34.

Further, the plate-like portion 1B is different from the conventional plate-like portion 60 in view of arranging way of the exhaust holes (34, 35) and the shape thereof, and in this embodiment, four or more exhaust holes (34, 35) are formed in a honeycomb shape. That is, a lot of (for example, six) exhaust holes 35 surrounding the exhaust hole 34 have the same shape, and the exhaust hole 35 is set smaller than an area of the exhaust hole 34. The exhaust hole 35 is formed approximately in an isosceles trapezoidal shape (in this case, a bottom line 35a is not a straight line but is formed in a circular arc shape) in a plan view.

Figure 7:
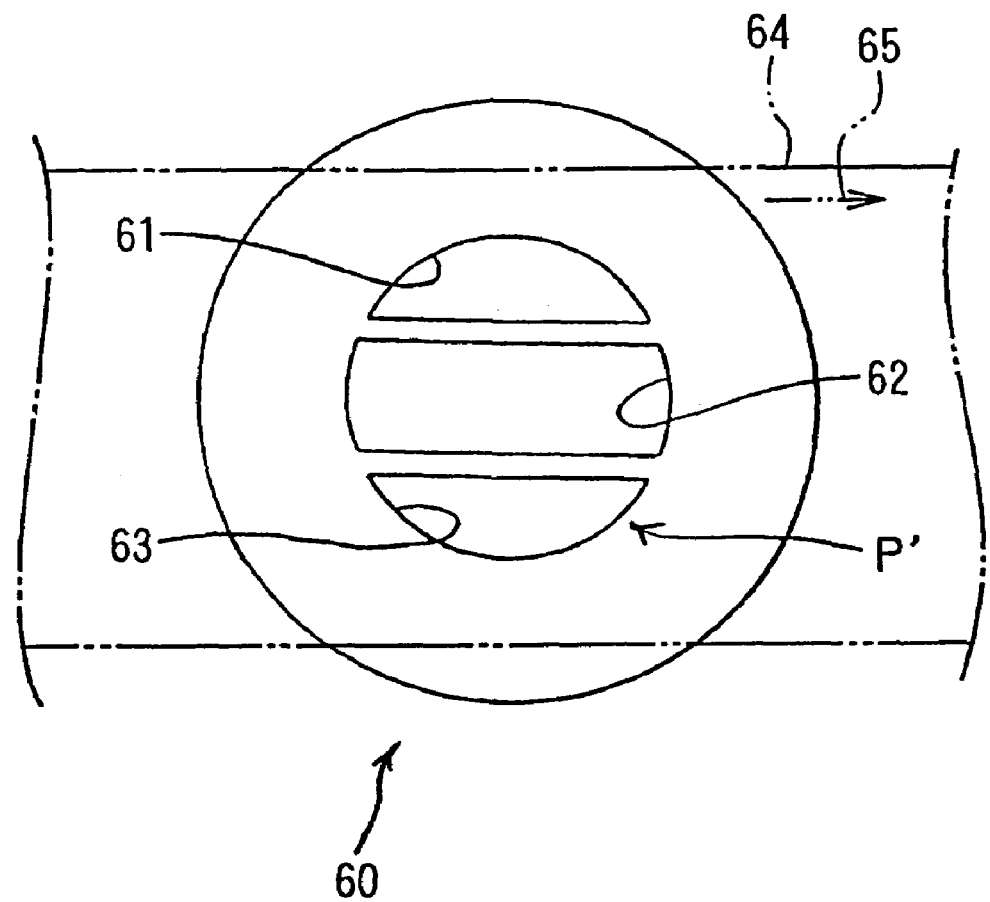
FIG. 7 shows a plan view of a conventional plate-like portion and a conventional filter tape in another embodiment.

Further, in four or more exhaust holes (34, 35) the central exhaust hole 34 positioned in the center and is formed in a regular hexagonal shape in a plan view. In contrast, in the three exhaust holes 61, 62 and 63 shown in FIG. 7, the exhaust hole 62 positioned in a center is formed in an approximately rectangular oblong hole in a plan view elongated in a take-up direction 65, and an area of two exhaust holes 61 and 63 formed in the same arcuate shape and formed so as to clamp the exhaust hole 62 is set smaller than the exhaust hole 62. Further, each of four or more exhaust holes (34, 35) has a smaller area than that of the exhaust holes 61 and 63.

The collecting region 33 mentioned above is constituted of central collecting region portion 33a, and peripheral collecting region portions 33b formed at the corresponding positions to the central exhaust hole 34 and peripheral exhaust holes 35. The collecting region portions (33a, 33b) are formed by the sample gas A' being drawn by the sampling pump, passing through the filter tape 5 from the upper face side to the under face side and further through four or more exhaust holes (34, 35) and being kept passing for a fixed time (for example, one hour). However, since each of the exhaust holes (34, 35) has the area smaller than that of the exhaust holes 61 and 63, the degree of the collapse to the under face side (another face side) generated by drawing each of the collecting region portions (33a, 33b) by the sampling pump 13 can be made smaller than that of the case of using the conventional plate-like portion 60.

The support means 1A of the structure mentioned above is operated in the following manner. That is, in a state that both clamping means 39 and 40 are separated, the roll-shaped filter tape 5 before adsorbing the PM 6 set in the supply reel 3 is reeled out from the supply reel 3 at a fixed length. Next, when the actuator tilts the separation levers 46 and 47 in a clockwise direction, the lower clamping means 39 is fitted to the upper clamping means 40 by a spring, and the filter tape 5 is clamped between both clamping means 39 and 40 while forming the deformed portion 5a.

Further, the PM is adsorbed to the fed-out filter tape 5 within the chamber 2, so that the collecting region 33 is formed. At this time, the collecting region 33 is formed and measured in a state in which the filter tape 5 is completely stopped. In the measurement mentioned above, the beta rays are irradiated onto the collecting region 33 from the beta-ray source 7, and the concentration of the PM is calculated in accordance with the arithmetical operation already described in detail.

Meanwhile, if the filter tape 5 is constituted only of the porous film 37 which is small in thickness, for example, 80 to 90 μm, is small in weight, for example, 0.3 mg/cm² and is made of fluorine resin, the filter tape 5 is improper for being continuously measured due to a weak (tensile) strength. That is, in the present embodiment, since the filter tape 5 is constituted such that the heavy reinforcing layer 38 having the weight, for example, 1.2 mg/cm² (average value) is bonded to the light and thin porous film 37, it is possible to improve the (tensile) strength of the filter tape 5 while reducing the thickness of the filter tape itself.

Further, since the reinforcing layer 38 is arranged in one face side 5A (the upper face side) of the filter tape 5 and the porous film 37 is arranged in another face side 5B (the under face side), it is possible to fix the position of the porous film 37 in a state in which the porous film 37 is clamped between the reinforcing layer 38 and the plate-like portion 1B. Accordingly, the collecting region 33 can be more clearly formed and the reproducibility is improved.

Further, since the porous film 37 is partially attached to the reinforcing layer 38, it is possible to make the thickness of the portion to which the reinforcing layer 38 is not attached small, or about about 80 to 90 μm, restricting the weight, for example, to about 0.3 mg/cm², and restricting the weight (density) of the filter tape 5 to about 1.5 mg/cm² on average, so that it is possible to reduce the beta-ray absorbing amount by the porous film 37. Accordingly, the sensitivity of measurement is improved.

Further, the plate-like portion 1B has four or more exhaust holes (34, 35) formed in the honeycomb shape. However, the size of the exhaust holes (34, 35) is smaller than the exhaust holes 61, 62 and 63 of the conventional plate-like portion 60, and since the (tensile) strength of the filter tape 5 is improved by using the heavy reinforcing layer 38 in comparison with the porous film 37, it is possible to make the degree of collapse of each of the collecting region portions (33a, 33b) to the under face side (another face side) generated by being drawn in by the sampling pump smaller than the case of using the conventional plate-like portion 60. Accordingly, measurement results are more reproducible.

As described above, in accordance with the first aspect of the present invention, it is possible to provide a PM concentration measuring apparatus that can carry out sensitive measurements of the PM using filter tape.

Figure 8:
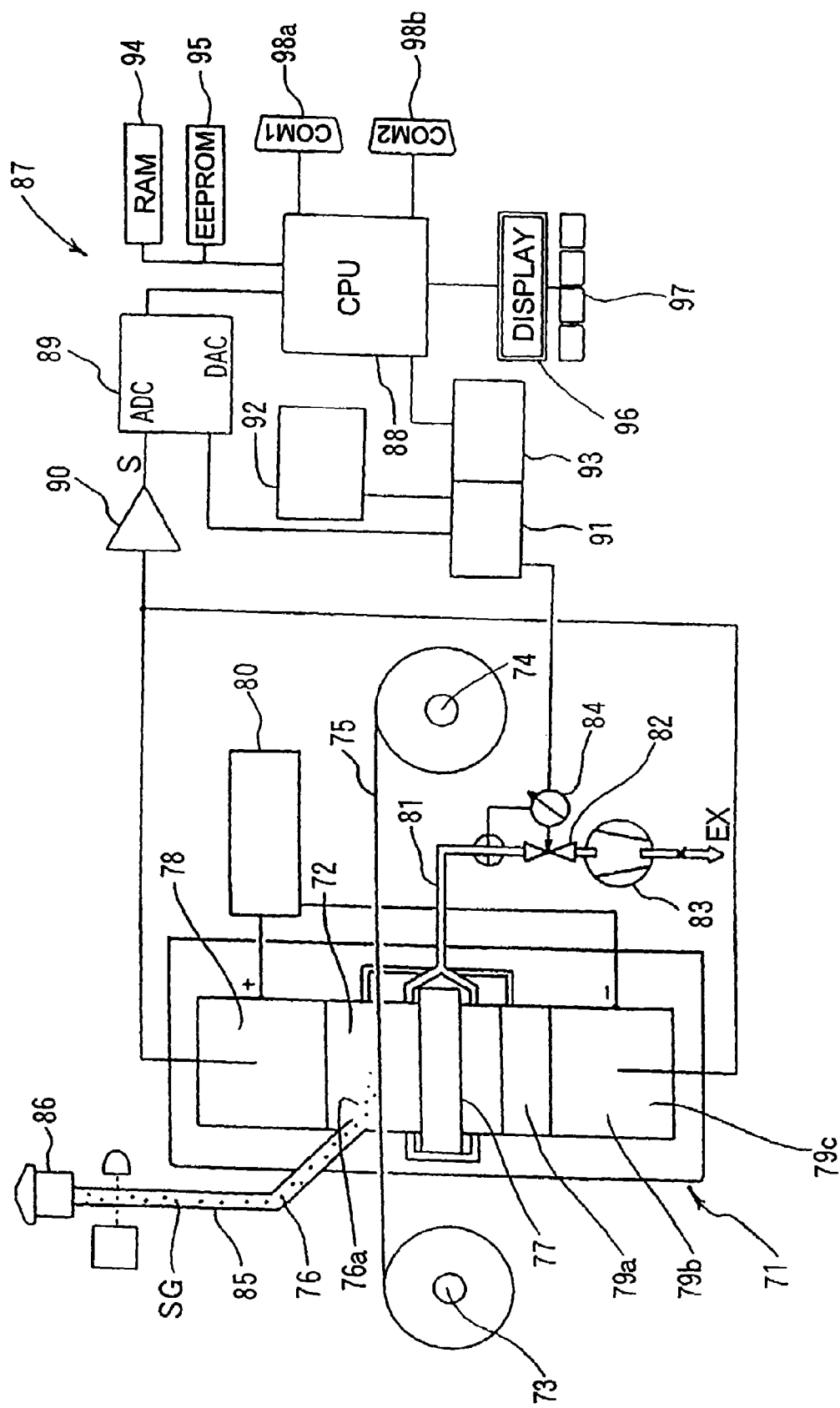
FIG. 8 schematically shows one embodiment of a structure of a PM concentration measuring apparatus in accordance with the second aspect of the present invention.

A description will be given in detail below of a second aspect of the present invention with reference to the accompanying drawings. FIG. 8 is a view schematically showing one example of a structure of a PM concentration measuring apparatus in accordance with this aspect. In this drawing, reference numeral 71 denotes a measuring apparatus main body. The measuring apparatus main body 71 is constituted as follows. Reference numeral 72 denotes a vacuum chamber. A ribbon filter 75 corresponding to a collecting means with a suitable width which is reeled out from a supply reel 73 and is taken up around a take-up reel 74 runs through an inner portion of the chamber 72, a beta-ray source 77 irradiating beta rays onto an accumulated layer 76a of a PM 76 collected on one face (an upper face) of the ribbon filter 75 is provided in one side (a lower side) of the ribbon filter 75, and a detector 78 detecting the beta rays passing through the accumulated layer 76a is provided in another side (an upper side) thereof. The detector 78 is constituted, for example, of a proportional counter, is provided with a function of detecting alpha rays as well as outputting the signal in correspondence to the strength of the detected beta rays, and outputs signals in correspondence to the strength of the detected alpha rays, whereby a concentration of the PM 76 can be measured in accordance with a beta-ray absorbing method, and the strength of the alpha rays can also be measured. In this case, reference symbols 79a and 79b denote a compensation chamber. Reference numeral 80 denotes a power source applying a predetermined d.c. voltage to a portion between the detector 78 and the compensation chamber 79b.

Further, reference numeral 81 denotes an exhaust system for exhausting the chamber 72 and the compensation chamber 79a in a predetermined vacuum state. The exhaust system 81 is connected to a vacuum pump 83 via a gas flow rate regulator 82, and is provided with a gas flow rate meter 84 measuring a flow rate of a sample gas SG.

Further, reference numeral 85 denotes a sampling tube supplying a fixed flow rate of sample gas SG to the vacuum chamber 72. A sizing device 86 is provided at the upstream end of the sampling tube 85. The sizing device 86 is structured so as to classify the PM 76 contained in the sample gas SG drawn into the sampling tube 85, thereby collecting the PM having a particle diameter more than a predetermined particle diameter and passing only the PM having a particle diameter equal to or less than the predetermined particle diameter through to the side of the vacuum chamber 72.

Reference numeral 87 denotes an arithmetical control portion controlling the measuring apparatus main body 71 and processing the signals from the side of the measuring apparatus main body 71. Reference numeral 88 denotes a CPU performing various kinds of arithmetical operations. Reference numeral 89 denotes a signal converter which converts an analogue signal into a digital signal and converting a digital signal into an analogue signal. Reference numeral 90 denotes an amplifier to which an output of the detector 78 is input. Reference numeral 91 denotes an analogue I/O to which detected outputs from the gas flow rate meter 84 and the other sensor 92 are input. Reference numeral 93 denotes a digital I/O. Reference numeral 94 denotes a Random Access Memory (RAM). Reference numeral 95 denotes an electrically erasable programmable (EEPROM). Reference numeral 96 denotes a display for displaying an arithmetical result and the like. Reference numeral 97 denotes an input keypad. Finally, reference symbols 98a and 98b denote COM1 and COM2 corresponding to communication ports for communicating with an external terminal.

A description will be given of an operation of the PM concentration measuring apparatus having the structure mentioned above. When turning on the vacuum pump 8, the sample gas SG is drawn into the sampling tube 85 via the sizing device 86. At this time, in the PM contained in the sample gas SG drawn into the sampling tube 85, the PM having the particle diameter larger than the predetermined particle diameter is removed, and the sample gas SG containing the PM having the particle diameter equal to or less than the predetermined particle diameter (hereinafter, refer to as the sized PM) is moved to the downstream side (the side of the vacuum chamber 72).

Thereafter, the sample gas SG containing the sized PM is introduced into the vacuum chamber 72 via the sampling tube 85, and passes through the ribbon filter 75. However, at this time, the sized PM is accumulated in a region shape on an upper surface of the ribbon filter 75, and forms an accumulated layer 76a. When the beta rays are irradiated onto the accumulated layer 76a from the beta-ray source 77, the beta rays are exposed to the absorption by the sized PM and the ribbon filter 75. However, the transmitted beta rays are detected by the detector 78. A signal A in proportion to the alpha rays is included in the signal S output from the detector 78 in addition to a signal B in proportion to the received beta rays, and this signal S is input to the CPU 88 via the amplifier 90 and the signal converter 89.

Figure 9:
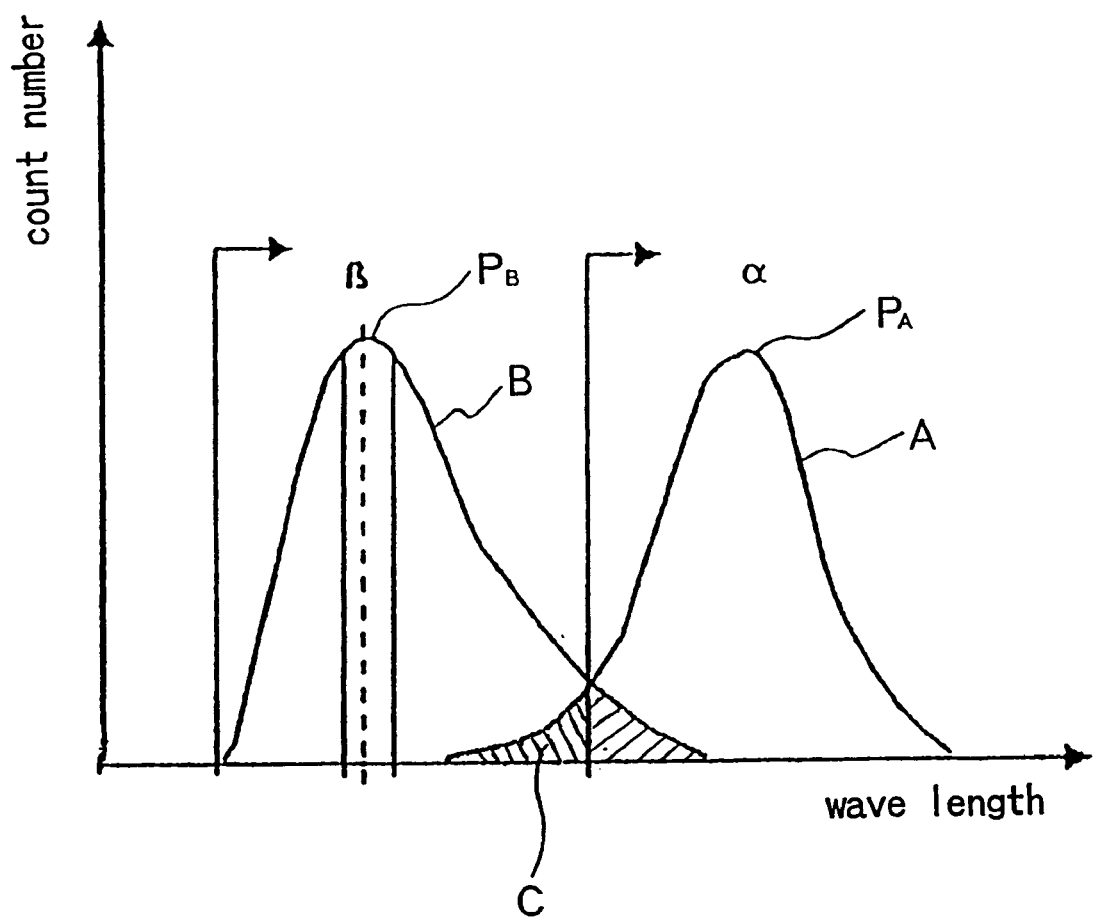
FIG. 9 is a view showing a state of distribution in which alpha rays and beta rays detected by a proportional counter.

In the CPU 88 mentioned above, first, a correction coefficient $F_1$ is prepared on the basis of calculation by using the amount of the alpha rays included in the signal S from the detector, and an amount of the alpha rays (radon gas) shown by reference symbol C in FIG. 9 is calculated by using the correction coefficient $F_1$. Further, since the transmitted beta rays existing in nature are included in the signal S, a correction coefficient $F_2$ is calculated by using the amount of the naturally occurring alpha rays and beta rays detected. This correction is a compensation for any errors caused by the presence of the naturally occurring alpha rays and beta rays, and provides high accuracy in accordance with the second aspect of the present invention.

Thereafter, the error values respectively caused by the alpha rays and the beta rays are cancelled by subtracting the error values from the amount of the transmitted beta rays obtained by the detector, and the amount of the transmitted beta rays after correction is determined. In accordance with this structure, it is possible to remove the error influence caused by the naturally occurring alpha rays and the beta rays, and it is possible to obtain a value of transmitted beta rays with high accuracy in the PM concentration measuring apparatus of the beta ray absorbing type. In order to determine mass m [μg] of the PM attached to the ribbon filter 75 from the value of the transmitted beta rays, the following known arithmetic expression (1) is used:

$$m = F \times \ln (R_o/R) \tag{1}$$

in which, $R_o$: beta-ray scattering strength of empty ribbon filter [I/s]

R: beta-ray scattering strength of ribbon filter after collecting PM [I/s]

F: calibration factor [μg/m$^3$]

The calibration factor F is a factor for converting the beta-ray scattering strength into the mass of the PM, and can be expressed by the formula $F = A/(\mu/\rho)$. In this case, A [cm$^2$] is a measured cross sectional area [cm$^2$] of the ribbon filter, and μ/ρ [cm/mg] is a specific mass decay factor [cm/mg] of the beta-ray source 77.

A PM concentration B [μg/m$^3$] can be obtained by compensating the mass of the PM determined by the expression (1), and the flow rate and the pressure of the sample gas SG.

When PM is trapped in the filter tape collecting region, the flow resistance through the filter tape is increased. The change in pressure due to the accumulated PM results in a detectable pressure loss.

The amounts of the alpha rays and the beta rays existing in nature differ according to place and time. The amount of the transmitted beta rays from which the error influences of the alpha rays and the beta rays existing in nature are removed can be obtained by continuously measuring not only the beta rays but also the alpha rays by the detector used for the measurement in accordance with the beta-ray absorbing method, determining the amount of the alpha rays in the portion, applying the influence to the detected value of the beta rays used for an essential measurement from the measured alpha rays, calculating the amount of the beta rays existing in nature on the basis of the amount of the alpha rays, and subtracting the error amounts applied to the amount of the transmitted beta rays caused by the alpha rays and the beta rays existing in nature from the amount of the transmitted beta rays, and the PM can be accurately measured by carrying out the arithmetic operation on the basis of the amount of the transmitted beta rays.

In more particular, when respectively setting the amount of the alpha rays and the amount of the beta rays existing in nature to Nα and Nβ, setting the sensitivity of the detector detecting the alpha rays to eff(α) and setting the sensitivity of the detector detecting the beta rays to eff(β), it is known that the following expression (2) is established.

$$N\alpha \cdot \text{eff}(\alpha) / N\beta \cdot \text{eff}(\beta) = 3.5 \tag{2}$$

The numerical value 3.5, Nα and Nβ are theoretically specified values. Accordingly, when setting the amount of the transmitted rays from which the error influences of the alpha rays and the beta rays existing in nature are removed to $R_1$, and respectively setting the measured amounts of the alpha rays and the beta rays to R(α) and R(β), the following expression (3) is established.

$$R_1 = R(\beta) - R(\alpha) \cdot 3.5 \tag{3}$$

Accordingly, the PM can be more accurately measured by compensating by using the expression (3) mentioned above.

Meanwhile, the detector 78 may employ the other radiation detector such as a scintillation detector, a semiconductor detector or the like.

As described above, in accordance with the second aspect of the present invention, since the structure is made such that the error influence caused by the alpha rays and the beta rays existing in nature can be removed from the detected value of the beta rays in the detector by using the amount of the alpha rays which is always detected by the detector, it is possible to obtain the result of measurement having a higher accuracy than the conventional one. Therefore, in accordance with the PM concentration measuring apparatus of this invention, it is possible to accurately measure even the minute PM contained at a reduced absolute amount such as the PM2.5.

Figure 10:
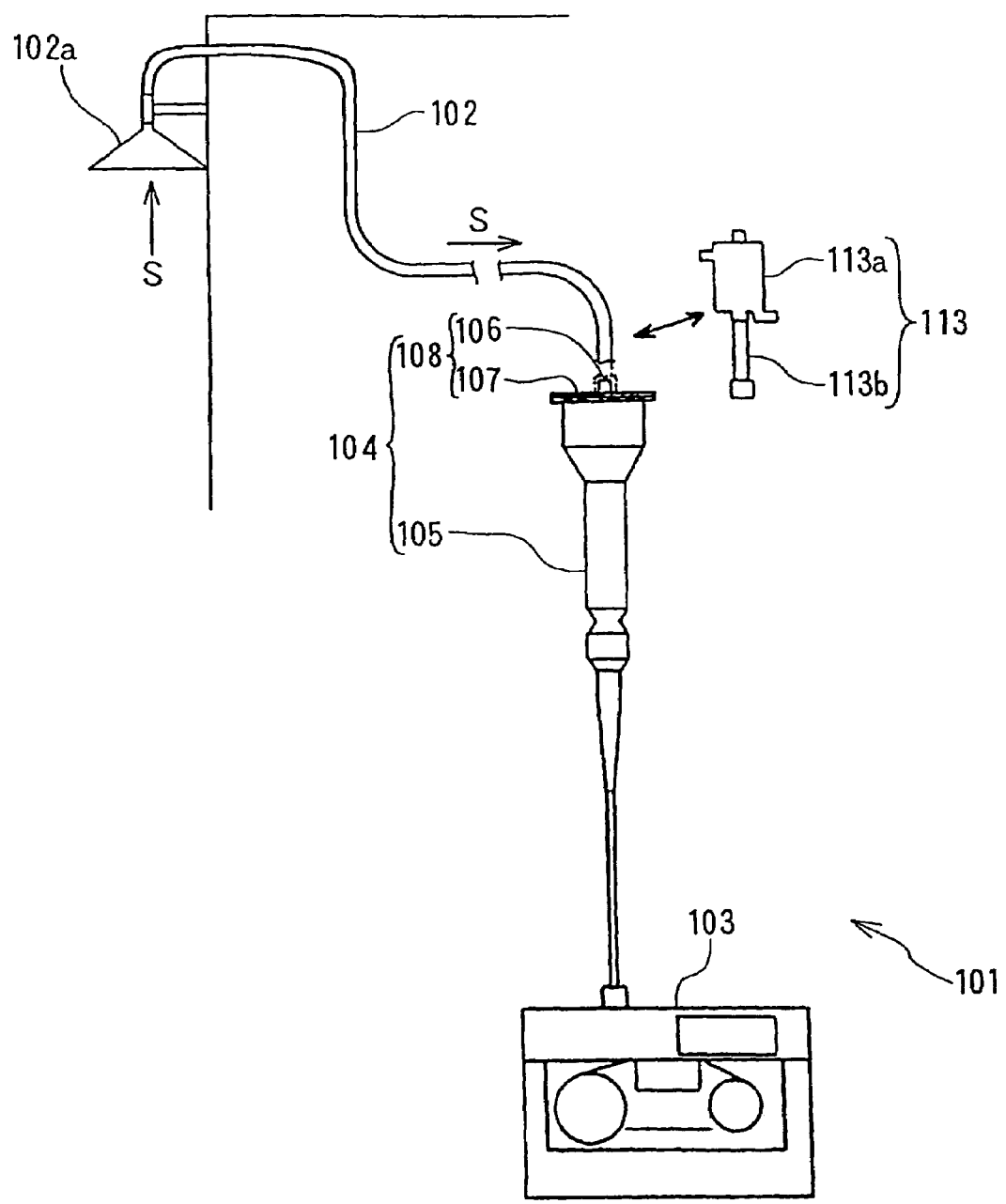
FIG. 10 shows an entire structure of a PM concentration measuring apparatus in accordance with the third aspect of the present invention.
Figure 15:
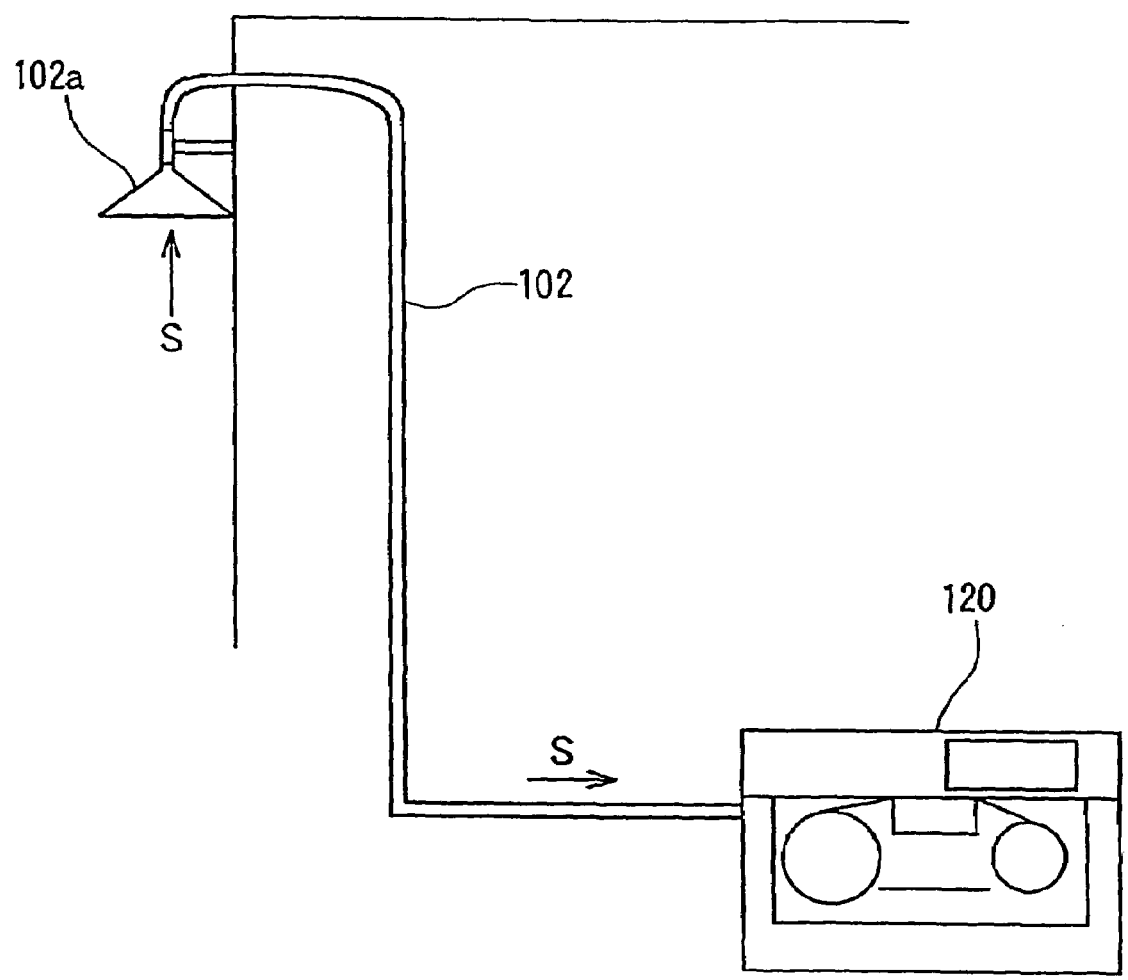
FIG. 15 shows an example of a conventional PM concentration measuring apparatus.
Figure 16:
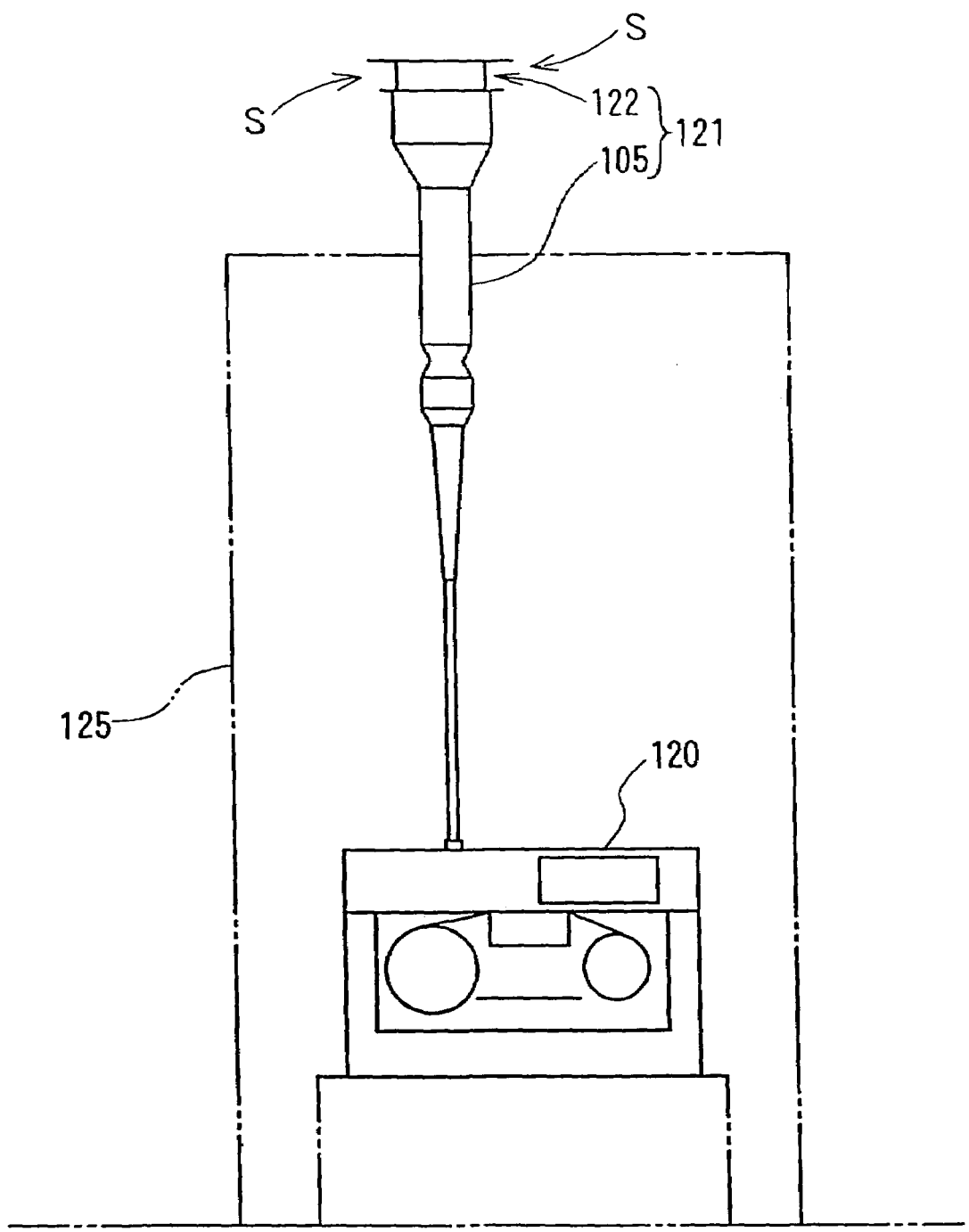
FIG. 16 shows another example of the conventional PM concentration measuring apparatus.
Figure 17:
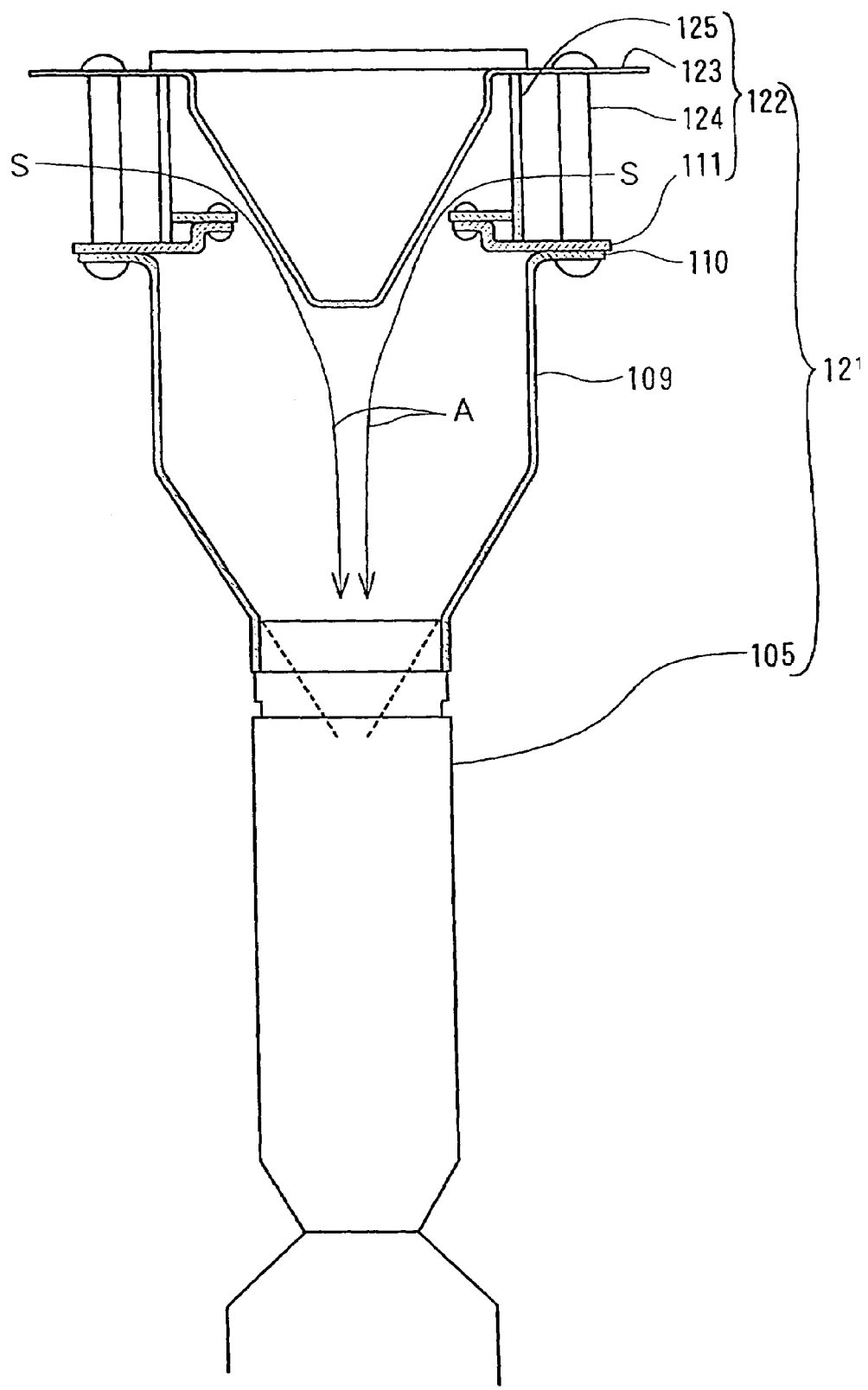
FIG. 17 shows an enlarged view of element 121 of an embodiment of the PM concentration measuring apparatus shown in FIG. 16.

FIG. 10 is a view showing an entire structure and a placing condition of a PM concentration measuring apparatus 101 in accordance with the third aspect of the present invention. In the following description, since portions denoted by the same reference numerals in FIGS. 15 to 17 are the same portions, a detailed description thereof here will be omitted.

According to FIG. 10, the PM concentration measuring apparatus 101, in accordance with the present embodiment, is constituted of an apparatus main body 103 having a measuring portion for the PM, and an impact type sampler (an impacter) 104 communicated with and connected to the apparatus main body 103. Further, the impacter 104 has a sizing device main body 105, and a sample introduction portion 108 (hereinafter, refer simply to as an introduction portion 108) constituted of a plate-like cover body 107 forming a pipe connection portion 106 in a center portion for introducing the sample gas S.

Figure 11:
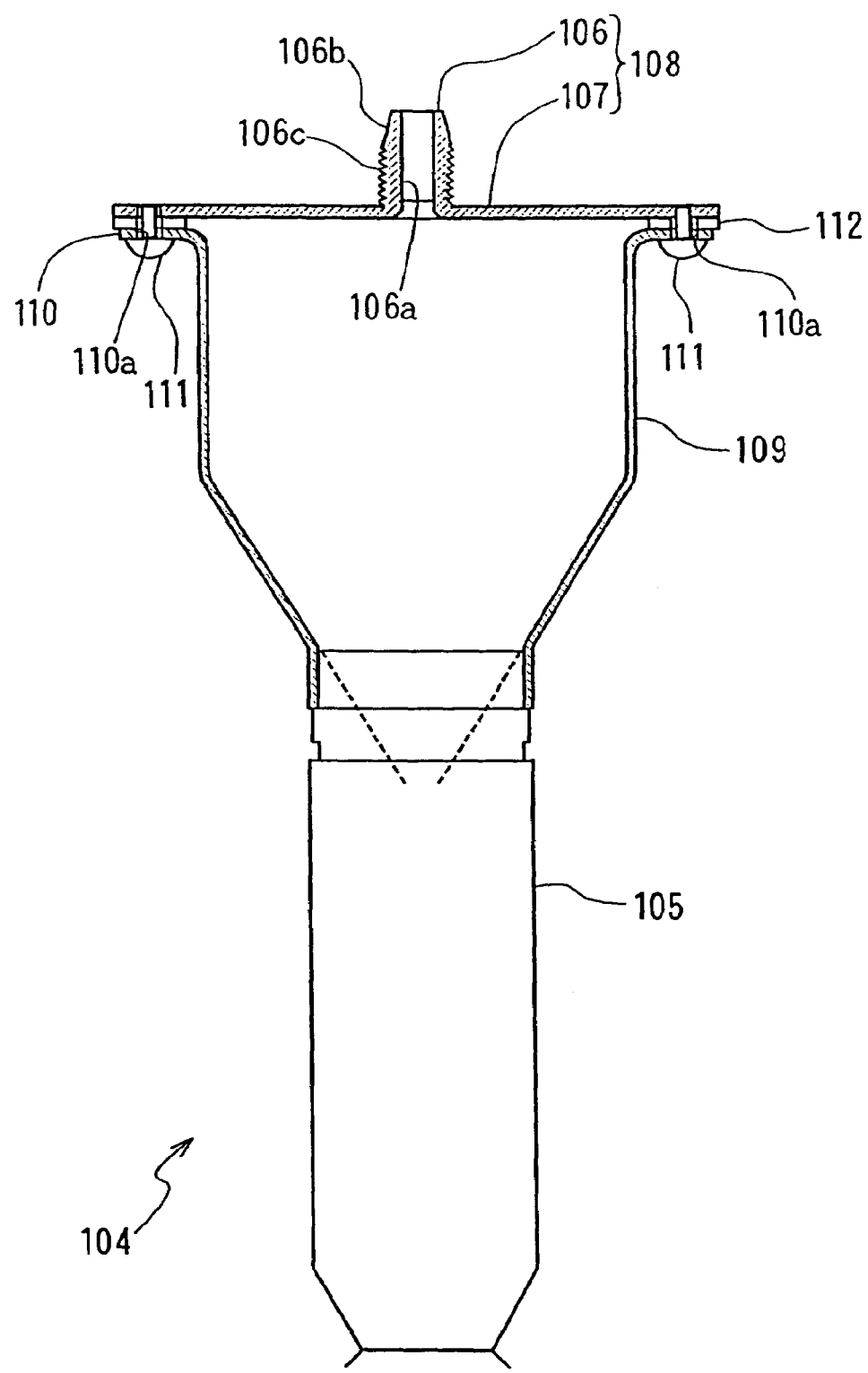
FIG. 11 shows an enlarged view of element 104 of an embodiment of the PM concentration measuring apparatus.
Figure 12:
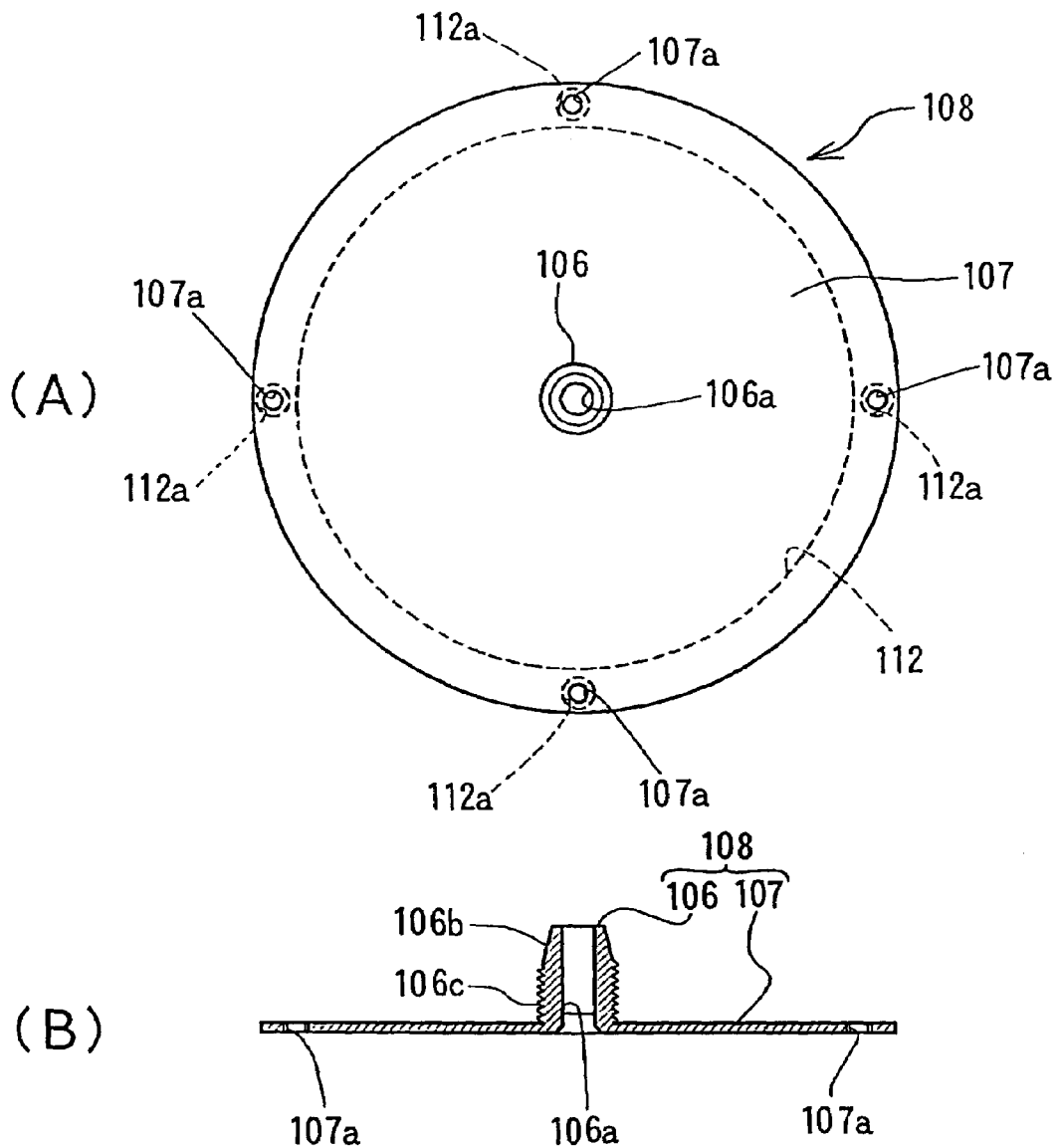

FIGS. 11 and 12 show an enlarged view of the structure of the introduction portion 108, in which FIG. 11 shows a state in which the introduction portion 108 is mounted to a mounting flange 110 of the sample intake port 109. Further, FIG. 12A is a plan view of the introduction portion 108, and FIG. 12B is a vertical cross sectional view. As shown in FIGS. 11 and 12, the cover body 107 is a plate body having approximately the same circular shape as an outer shape (a circular shape) of the mounting flange 110, and made, for example, of stainless steel. Further, female threaded holes 107*a* are formed near an outer peripheral portion of the cover body 107 at positions corresponding to four mounting holes 110*a* (illustrated in FIG. 11) formed near an edge portion of the flange 110, for example, at an interval of 90 degrees.

The pipe connection portion 106 has an approximately tubular shape integrally formed in such a manner so as to form a communication hole 106*a* in the center portion of the cover body 107 with a taper-shaped receiving port (hereinafter, refer to as a taper receiving port 106) in which a taper portion 106*b* is formed in an outer periphery of a leading end portion and a concavo-convex male threaded portion 106*c* is formed on an outer periphery of a base end portion.

Accordingly, it can be fixed by fastening with screws 111 (illustrated in FIG. 11) in such a manner that a position of a mounting female threaded hole 107*a* of the flange 110 is aligned with a position of the mounting hole 110*a*, as well as an open end of the sample intake port portion 109 formed by taking out the introduction portion 122 of the conventional impacter 121 shown in FIG. 17 is structured such as to be enclosed by the cover body 107 of the introduction portion 108. In this case, reference numeral 112 denotes a circumferential band-shaped packing interposed between the flange 110 and the cover body 107, and an opening portion 112*a* (illustrated in FIG. 12) is formed in this packing 112 at a position corresponding to the mounting female threaded hole 107*a*.

The sampling pipe 102 connected to the taper receiving port 106 can be easily attached to and detached from the sizing device main body 105 by mounting the introduction portion 108 having the structure mentioned above in place of the introduction portion 122 of the impacter 121 to the sizing device main body 105. Meanwhile, since the taper receiving port 106 forms the taper portion 106*b* in the leading end portion thereof, it is possible to easily connect the sampling pipe 102 to the taper receiving port 106. Above all, in the case that the sampling pipe 102 is formed by a hose made of a flexible synthetic resin, no tools are required to connect the sampling pipe 102 to the taper receiving port 106, and the connection may be made with only bare hands.

Further, since the concavo-convex male threaded portion 106*c* is formed in the outer periphery of the base end portion in the taper receiving port 106, it is possible to prevent the once mounted sampling pipe 102 from accidentally coming off. That is, in the PM concentration measuring apparatus 101, since no great pressure is applied to the connection portion between the taper receiving port 106 and the sampling pipe 102, a simple connection mentioned above between the taper receiving port 106 and the sampling pipe 102 is sufficient, so that it is useful in achieving an improvement of attaching and detaching operationality of the sampling pipe 102 to set the structure of the pipe connection portion 106 to the taper receiving port.

Further, since the sample gas S within the sampling pipe 102 is the outdoor air, a leak or the like generated in the taper receiving port 106 creates no problem. Accordingly, it is sufficient that the structure of the pipe connection portion 106 is constituted by the taper-shaped receiving port which is easily attached and detached. However, the structure may be made such that a fastening member fastening the sampling pipe 102 from a further outer periphery is provided after mounting the sampling pipe 102 to the taper receiving port 106, thereby preventing the sampling pipe 102 from becoming detached from the taper receiving port 106.

As is apparent from a comparison between the PM concentration measuring apparatus 101 as shown in FIG. 10, and the PM concentration measuring apparatus 120 shown in FIG. 15, the PM concentration measuring apparatus 101 having the impacter 104 forming the taper receiving port 106 can be arranged in place of the conventional PM concentration measuring apparatus 120 which is already placed. That is, no major placing work is required for corresponding to the change in specification of the sizing device in the PM concentration measuring apparatus for measuring the concentration of the PM, and it is possible to easily switch into the measurement which corresponds to "Preliminary Manual for Method of Measuring Mass Concentration of Particulate Matter (PM2.5) in Atmosphere" defined by the Japanese Environmental Agency.

In addition, in FIG. 10, reference numeral 113 denotes a filter unit which is detachably mounted to the taper receiving port 106, reference symbol 113*a* denotes a filter main body, for example, in which an HEPA filter is built, reference symbol 113*b* denotes a hose made of a synthetic resin and serving as a flexible pipe for circulating the atmosphere filtered by using the HEPA filter.

That is, the sample gas containing no dust can be introduced into the impacter 104 by mounting the filter unit 113 to the taper receiving port 106. Namely, in order to carry out the base line test as a basic instruction (confirmation of noise) in a non-dust state corresponding to an important test for confirming a basic performance of the PM concentration measuring apparatus 101, the operator only detaches the sampling pipe 102 from the taper receiving port 106 and connects the flexible pipe 113b of the filter unit 113 to the taper receiving port 106.

Accordingly, it is not difficult to detach the impacter 104 from the apparatus main body 103 as is required at the time of carrying out the base line test. Meanwhile, a flow passage switching valve may be provided in the PM concentration measuring apparatus 101 in an upstream side or a downstream side of the impacter 104. In this case, it is possible to freely switch the drawing of the sample gas via the filter unit 113 and drawing of the sample gas without the filter unit 113.

Figure 13:
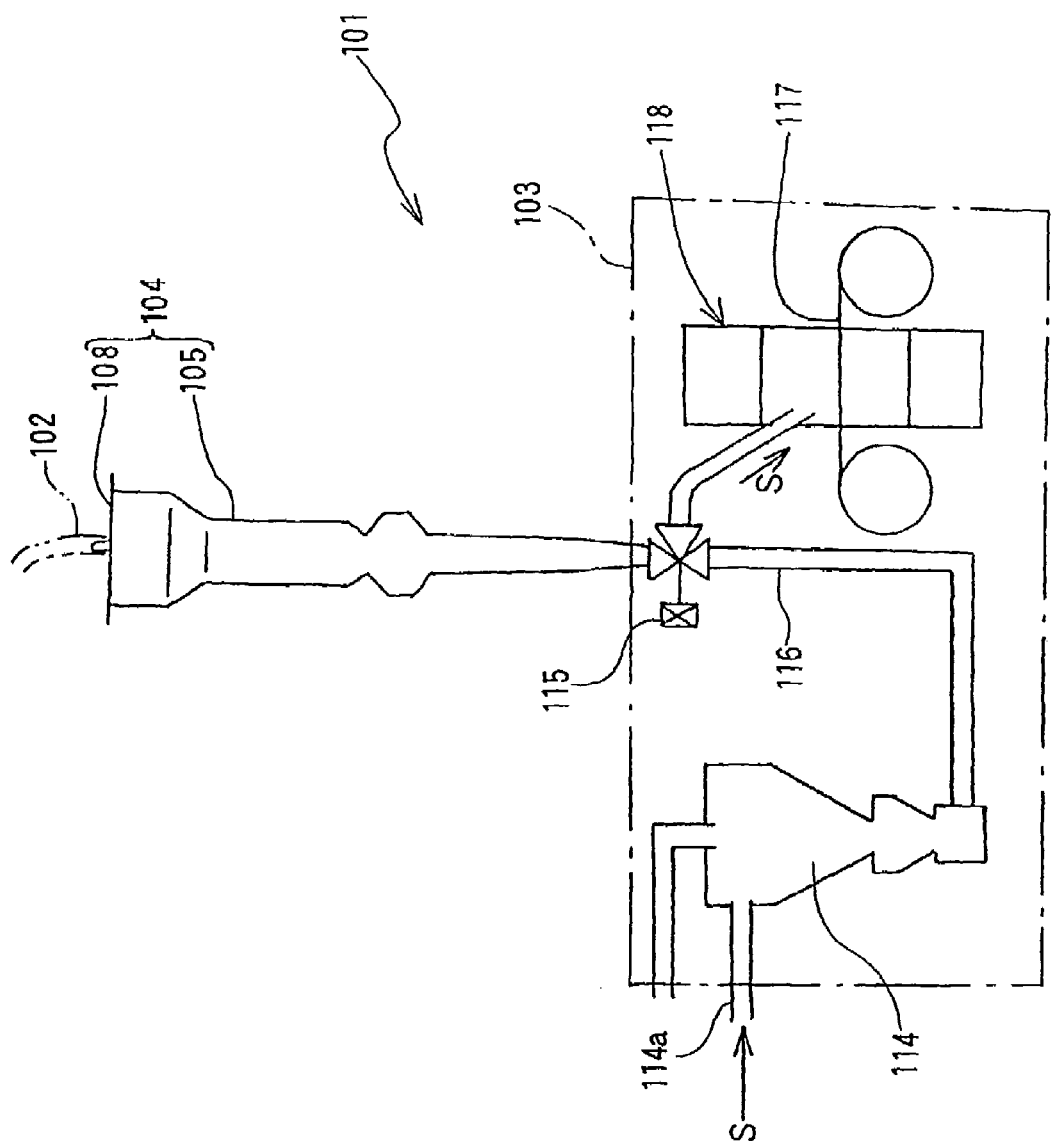
FIG. 13 shows a block diagram abstraction of the PM concentration measuring apparatus.

FIG. 13 is a view schematically showing an entire structure of the PM concentration measuring apparatus 101. In FIG. 13, reference numeral 114 denotes a cyclone type sampler (a cyclone) built in the PM concentration measuring apparatus 101. A pipe 116 for detachably connecting the impacter 104 to a downstream side of the cyclone 114, for example, via an electromagnetic valve 115 is formed. Further, reference numeral 117 denotes a tape-like filter for collecting the PM contained in the sample gas S, and reference numeral 118 denotes a measuring portion measuring an amount of the PM collected in the filter 117 in accordance with a beta-ray absorption method. Accordingly, the PM concentration measuring apparatus 101 carries out the PM concentration measurement using the same cyclone 114 as the conventional one as the sizing device by connecting the sampling pipe 102 to the inflow port of the cyclone 114 and switching the electromagnetic valve 115. That is, it is possible to flexibly adapt to an improvements in the measuring methods of the PM concentration.

Figure 14:
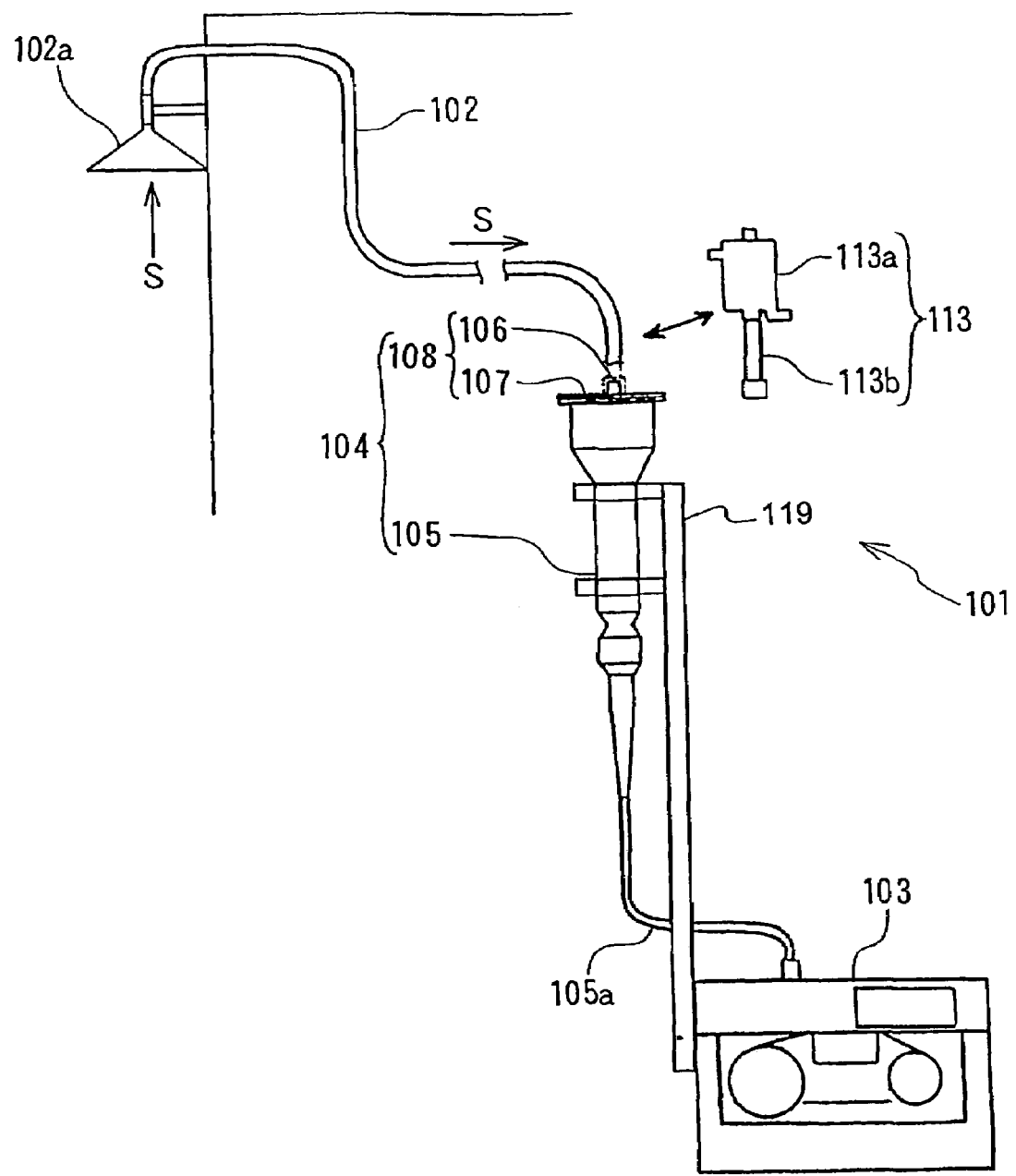
FIG. 14 shows an alternative embodiment of the PM concentration measuring apparatus.

FIG. 14 is a view showing a modified embodiment of the PM concentration measuring apparatus mentioned above. In FIG. 14, reference numeral 119 denotes a holder fixed to a side portion of the measuring apparatus main body 103, and reference symbol 105a denotes a pipe communicated with and connected to the measuring apparatus main body 103 from the sizing device main body 105. That is, it is possible to restrict the height of the PM concentration measuring apparatus 101 low by mounting the impacter 104 by means of the holder 119, whereby it is possible to achieve a compact structure, and it is possible to easily arrange the PM concentration measuring apparatus 101 in the room.

As described above, in accordance with the PM concentration measuring apparatus of the third aspect of the present invention, not only it is possible to size the PM using the impact type sampler with ease, but also the base line test can be easily carried out by mounting the filter to the impact type sampler with ease.

Those skilled in the art will appreciate that various adaptations and modifications of the just-described preferred embodiment can be configured without departing from the scope and spirit of the invention. Therefore, it is to be understood that, within the scope of the amended claims, the invention may be practiced other than as specifically described herein.

What is claimed is:

1. In a particulate matter concentration measuring apparatus for continuously measuring a concentration of particulate matter in a sample gas collected in a collecting region formed on a collecting member, the collecting region being formed by drawing the sample gas through a cross-sectional area of the collecting member from one face side to the other face side, wherein
the collecting member is a filter tape roll, the filter tape roll includes a porous film made of a fluorine resin for trapping particulate matter in the collecting region, the filter tape roll includes a reinforcing layer of a non-woven fabric on the porous film, the reinforcing layer allows the transmission of the sample gas and enables sufficient strength for movement of a portion of the filter tape relative to the collecting region to provide a sequential series of measurements at spaced positions along the filter tape, and
a supporting means for supporting a portion of filter tape unwound from the filter tape roll in the collecting region, the supporting means having a plurality of exhaust holes for discharging the sample gas passing through the portion of filter tape and supporting the portion of filter tape against being deformed in the collecting region, the supporting means having one exhaust hole at a central position and at least three exhaust holes at a peripheral portion.

2. The particulate matter concentration measuring apparatus of claim 1,
wherein the particulate matter concentration is measured using a beta-ray absorbing method.

3. The particulate matter concentration measuring apparatus of claim 2,
wherein the particulate matter concentration measurement includes a compensation for any error caused by naturally occurring alpha and beta radiation.

4. The particulate matter concentration measuring apparatus of claim 1,
wherein the particulate matter concentration is measured using a pressure loss method.

5. The particulate matter concentration measuring apparatus of claim 1,
wherein the filter tape roll presents the porous film on one face side and presents the reinforcing layer on another face side.

6. The particulate matter concentration measuring apparatus of claim 1,
wherein the reinforcing layer comprises a non-woven fabric having a low hygroscopic property.

7. The particulate matter concentration measuring apparatus of claim 1,
wherein the reinforcing layer is a non-woven fabric selected from the group consisting of polyethylene, polyethylene terephthalate, nylon, polyester and polyamide.

8. The particulate matter concentration measuring apparatus of claim 1,
wherein the supporting means includes a thin plate-like portion within which the plurality of exhaust holes are formed in a honeycomb shape.

9. In a particulate matter concentration measuring apparatus for continuously measuring a concentration of particulate matter in a sample gas collected in a collecting region formed on a collecting member, the collecting region being formed by drawing the sample gas through a cross-sectional area of the collecting member from one face side to the other face side, wherein
the collecting member is a filter tape roll, the filter tape roll includes a porous film made of a fluorine resin for trapping particulate matter in the collecting region, the filter tape roll includes a reinforcing layer of a non-woven fabric on the porous film, the reinforcing layer allows the transmission of the sample gas and enables sufficient strength for movement of a portion of the filter tape relative to the collecting region to provide a sequential series of measurements at spaced positions along the filter tape;

an impact type sampler for performing a filtering of particulate matter in a sample gas by removing from the sample gas the particulate matter having a large particle diameter on the basis of collisions within the sample gas and selectively sampling the particulate matter having a small particle diameter prior to collection of the particulate matter in the collecting region, the impact type sampler having a sample intake portion, including a raised connection portion on an upper surface of the impact type sampler to enable a removable attachment to an atmospheric air introduction portion for introducing the sample gas, the impact type sampler having an output port for conducting a filtered sample gas to the collecting region, the impact type sampler being detachably connected to the particulate matter concentration measuring apparatus; and a conduct in communication with the atmospheric air introduction portion, the conduct is removably connected with the sample intake portion through the raised connection portion wherein the sample gas is a predetermined portion of atmospheric air.

10. The particulate matter concentration measuring apparatus of claim 9 further comprising:

a dust removing filter for removing dust from the sample gas, the dust removing filter being detachably mounted to the raised connection portion so as to remove dust from the sample gas prior to introduction of the sample gas into the impact type sampler.

11. The particulate matter concentration measuring apparatus of claim 9 wherein the impact type sampler includes a funnel-shaped sample intake portion, a cover plate extending across the sample intake portion to form the upper surface with the raised connection portion, and a sizing device main body.

12. The particulate matter concentration measuring apparatus of claim 11 wherein the raised connection portion, funnel-shaped sample intake portion and the sizing device main body are located coaxially to a vertical axis of the raised connection portion.

13. The particulate matter concentration measuring apparatus of claim 12 further comprising:

a dust removing filter for removing dust from the sample gas, the dust removing filter being detachably mounted to the raised connection portion so as to remove dust from the sample gas prior to introduction of the sample gas into the impact type sampler.

14. In a particulate matter concentration measuring apparatus for continuously measuring a concentration of particulate matter in a sample gas collected in a collecting region formed on a collecting member, the collecting region being formed by drawing the sample gas through a cross-sectional area of the collecting member from one face side to the other face side, wherein the collecting member is a filter tape roll, the filter tape roll includes a porous film made of a fluorine resin for trapping particulate matter in the collecting region, the filter tape roll includes a reinforcing layer of a nonwoven fabric on the porous film, the reinforcing layer allows the transmission of the sample gas and enables sufficient strength for movement of a portion of the filter tape relative to the collecting region to provide a sequential series of measurements at spaced positions along the filter tape;

a supply reel for rotably mounting the filter tape roll;

a take-up reel for receiving the filter tape from teh supply reel; and a transfer sensor for detecting a dispensing of a fixed length of filter tape from the supply reel.

15. The particulate matter concentration measuring apparatus of claim 14 wherein the collecting region includes a support member that permits the transmission of the sample gas and a clamping member that can releasably hold a fixed length of filter tape to collect particulate matter from the sample gas, the clamping member is positioned between the supply reel and the take-up reel.

16. The particulate matter concentration measuring apparatus of claim 15 wherein the reinforcing layer has a weight of approximately 1.2 mg/cm$^2$.

17. The particulate matter concentration measuring apparatus of claim 16 wherein the porous film is approximately one-fourth the weight of the reinforcing layer.

18. In a particulate matter concentration measuring apparatus for continuously measuring a concentration of particulate matter in a sample gas collected in a collecting region formed on a collecting member, the collecting region being formed by drawing the sample gas through a cross-sectional area of the collecting member from one face side to the other face side, wherein the collecting member is a filter tape roll, the filter tape roll includes a porous film made of a fluorine resin for trapping particulate matter in the collecting region, the filter tape roll includes a reinforcing layer of a nonwoven fabric on the porous film, the reinforcing layer allows the transmission of the sample gas and enables sufficient strength for movement of a portion of the filter tape relative to the collecting region to provide a sequential series of measurements at spaced positions along the filter tape, and a supporting means for supporting a portion of filter tape unwound from the filter tape roll in the collecting region, the supporting means having a plurality of exhaust holes for discharging the sample gas passing through the portion of filter tape and supporting the portion of filter tape against being deformed in the collecting region, the support means having at least four exhaust holes, wherein the supporting means includes a first clamping means and a second clamping means which move together to securely hold the portion of filter tape at a time of collecting the particulate matter while permitting the passage of the sample gas through the portion of filter tape, the first clamping means and second clamping means being moved apart so as to release the portion of filter tape at a time of moving the portion of filter tape.

19. The particulate matter concentration measuring apparatus of claim 18, wherein a recess portion is formed in the first clamping means and a corresponding convex portion is formed in the second clamping means, the complementary recess and convex portions for preventing the portion of filter tape from being displaced during clamping.

20. In a particulate matter concentration measuring apparatus for continuously measuring a concentration of particulate matter in a sample gas collected in a collecting region formed on a collecting member, the collecting region being formed by drawing the sample gas through a cross-sectional area of the collecting member from one face side to the other face side, wherein the collecting member is a filter tape roll, the filter tape roll includes a porous film made of a fluorine resin for trapping particulate matter in the collecting region, the filter tape roll includes a reinforcing layer of a nonwoven fabric on the porous film, the reinforcing layer allows the transmission of the sample gas and enables sufficient strength for movement of a portion of the filter tape relative to the collecting region to provide a sequential series of measurements at spaced positions along the filter tape;

an impact type sampler for performing a filtering of particulate matter in a sample gas by removing from the sample gas the particulate matter having a large particle diameter on the basis of collisions within the sample gas and selectively sampling the particulate matter having a small particle diameter prior to collection of the particulate matter in the collecting region, the impact type sampler having a sample intake portion, the impact type sampler having an output port for conducting a filtered sample gas to the collecting region, the impact type sampler being detachably connected to the particulate matter concentration measuring apparatus;

a cyclone type sampler for filtering particulate matter in a sample gas using centrifugal separation of the particulate matter prior to collection of the particulate matter in the collecting region, the cyclone type sampler having an input port for admitting the sample gas and an output port for emitting a separated sample gas, the input port of the cyclone type sampler being connected to the source of the sample gas, the cyclone type sampler output port being connected to the particulate matter concentration measuring apparatus so as to conduct a second filtered sample gas to the collecting region, the cyclone type sampler being detachably connected to the particulate matter concentration measuring apparatus; and an electro-mechanical switch for selecting between the first filtered sample gas from the impact type sampler and the second filtered sample gas from the cyclone type sampler for conducting to the collecting region.

21. In a particulate matter concentration measuring apparatus for continuously measuring a concentration of particulate matter in a sample gas of atmospheric air collected in a collecting region formed on a collecting member, the collecting region being formed by drawing the sample gas through a cross-sectional area of the collecting member from one face side to the other face side, wherein the collecting member is a filter tape roll, the filter tape roll includes a porous film made of a fluorine resin for trapping particulate matter in the collecting region, the filter tape roll includes a reinforcing layer of a nonwoven fabric on the porous film, the reinforcing layer allows the transmission of the sample gas and enables sufficient strength for movement of a portion of the filter tape relative to the collecting region to provide a sequential series of measurements at spaced positions along the filter tape;

an impact type sampler for performing a filtering of particulate matter in a sample gas by removing from the sample gas the particulate matter having a large particle diameter on the basis of collisions within the sample gas and selectively sampling the particulate matter having a small particle diameter prior to collection of the particulate matter in the collecting region, the impact type sampler having a sample intake portion, the impact type sampler having an output port for conducting a filtered sample gas to the collecting region, the impact type sampler being detachably connected to the particulate matter concentration measuring apparatus; and a mounting flange for mounting a sample introduction portion to the sample intake portion of the impact type sampler, the sample introduction portion being a cover body having approximately the same outer shape as an outer shape of the mounting flange and forming a pipe connection portion in a center portion thereof, the pipe connection portion having a taper-shaped receiving port.

22. The particulate matter concentration measuring apparatus of claim 21, further comprising:

a dust removing filter for removing dust from the sample gas, the dust removing filter being detachably mounted to the pipe connection portion so as to remove dust from the sample gas prior to introduction of the sample gas into the impact type sampler.

* * * * *